(12) United States Patent
Ginn et al.

(10) Patent No.: US 7,931,669 B2
(45) Date of Patent: *Apr. 26, 2011

(54) INTEGRATED VASCULAR DEVICE WITH PUNCTURE SITE CLOSURE COMPONENT AND SEALANT AND METHODS OF USE

(75) Inventors: Richard S. Ginn, San Jose, CA (US); W. Martin Belef, San Jose, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 10/147,774

(22) Filed: May 17, 2002

(65) Prior Publication Data
US 2002/0133193 A1    Sep. 19, 2002

Related U.S. Application Data

(63) Continuation of application No. 09/610,238, filed on Jul. 5, 2000, now Pat. No. 6,391,048, which is a continuation-in-part of application No. 09/478,179, filed on Jan. 5, 2000, now Pat. No. 6,197,042.

(51) Int. Cl.
*A61B 17/04* (2006.01)
(52) U.S. Cl. .................. 606/213; 606/142; 606/151
(58) Field of Classification Search ............... 606/213, 606/142, 151, 157, 158, 139
See application file for complete search history.

(56) References Cited

U.S. PATENT DOCUMENTS

| 287,046 | A | 10/1883 | Norton |
|---|---|---|---|
| 438,400 | A | 10/1890 | Brennen |
| 1,088,393 | A | 2/1914 | Backus |
| 1,331,401 | A | 2/1920 | Summers |
| 1,426,111 | A | 8/1922 | Sacker |
| 1,516,990 | A | 11/1924 | Silverman |
| 1,596,004 | A | 8/1926 | De Bengoa |
| 1,647,958 | A | 11/1927 | Ciarlante |
| 1,847,347 | A | 3/1932 | Maisto |
| 1,852,098 | A | 4/1932 | Anderson |
| 1,880,569 | A | 10/1932 | Weis |

(Continued)

FOREIGN PATENT DOCUMENTS

AU    2003297432    12/2003

(Continued)

OTHER PUBLICATIONS

Database WPI; Section PQ, Week 200120; Derwent Publications Ltd., London GB; AN 2001-203165; XP002199926 & ZA 200 100 528 A (Anthony T), Feb. 28, 2001 abstract.

(Continued)

*Primary Examiner* — Julian W Woo
*Assistant Examiner* — Christina Lauer
(74) *Attorney, Agent, or Firm* — Workman Nydegger

(57) ABSTRACT

Apparatus and methods are provided for use in sealing a vascular puncture site. The invention comprises an integrated vascular device having a sheath with a closure component and puncture sealant. The closure component is disposed on and advanceable over the exterior of the sheath and may comprise any of a variety of apparatus suited for closing a vascular puncture. Once the closure component has been actuated to close the puncture, sealant is introduced to seal the puncture. The sheath and closure component are then removed from the patient.

20 Claims, 5 Drawing Sheets

U.S. PATENT DOCUMENTS

| | | |
|---|---|---|
| 2,075,508 A | 3/1937 | Davidson |
| 2,087,074 A | 7/1937 | Tucker |
| 2,108,206 A | 2/1938 | Meeker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Brainstetter |
| 3,814,104 A | 6/1974 | Irnich et al. |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,011,872 A | 3/1977 | Komiya |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,595,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |

| | | | | | | |
|---|---|---|---|---|---|---|
| 5,122,156 A | 6/1992 | Granger et al. | | 5,403,331 A | 4/1995 | Chesterfield et al. |
| 5,131,379 A | 7/1992 | Sewell, Jr. | | 5,409,499 A | 4/1995 | Yi |
| 5,147,381 A | 9/1992 | Heimerl et al. | | 5,411,520 A | 5/1995 | Nash et al. |
| 5,156,609 A | 10/1992 | Nakao et al. | | 5,413,571 A | 5/1995 | Katsaros et al. |
| 5,158,566 A | 10/1992 | Pianetti | | 5,413,584 A | 5/1995 | Schulze |
| 5,160,339 A | 11/1992 | Chen et al. | | 5,416,584 A | 5/1995 | Kay |
| 5,167,634 A | 12/1992 | Corrigan, Jr. et al. | | 5,417,699 A | 5/1995 | Klein et al. |
| 5,167,643 A | 12/1992 | Lynn | | 5,419,777 A | 5/1995 | Hofling |
| 5,171,249 A | 12/1992 | Stefanchik et al. | | 5,423,857 A | 6/1995 | Rosenman et al. |
| 5,171,250 A | 12/1992 | Yoon | | 5,425,489 A | 6/1995 | Shichman et al. |
| 5,171,251 A | 12/1992 | Bregen et al. | | 5,425,740 A | 6/1995 | Hutchinson, Jr. |
| 5,176,648 A | 1/1993 | Holmes et al. | | 5,431,639 A * | 7/1995 | Shaw .......................... 604/264 |
| 5,176,682 A | 1/1993 | Chow | | 5,431,667 A | 7/1995 | Thompson et al. |
| 5,176,691 A | 1/1993 | Pierce | | 5,433,721 A | 7/1995 | Hooven et al. |
| 5,192,287 A | 3/1993 | Fournier et al. | | 5,437,631 A | 8/1995 | Janzen |
| 5,192,288 A | 3/1993 | Thompson et al. | | 5,439,479 A | 8/1995 | Shichman et al. |
| 5,192,300 A | 3/1993 | Fowler | | 5,443,477 A | 8/1995 | Marin et al. |
| 5,192,301 A | 3/1993 | Kamiya et al. | | 5,443,481 A | 8/1995 | Lee |
| 5,192,302 A | 3/1993 | Kensey et al. | | 5,449,359 A | 9/1995 | Groiso |
| 5,192,602 A | 3/1993 | Spencer et al. | | 5,456,400 A | 10/1995 | Shichman et al. |
| 5,203,787 A | 4/1993 | Noblitt et al. | | 5,462,558 A | 10/1995 | Kolesa et al. |
| 5,209,756 A | 5/1993 | Seedhorm et al. | | 5,462,561 A | 10/1995 | Voda |
| 5,217,024 A | 6/1993 | Dorsey et al. | | 5,466,241 A | 11/1995 | Leroy et al. |
| 5,217,471 A | 6/1993 | Burkhart | | 5,470,010 A | 11/1995 | Rothfuss et al. |
| 5,219,359 A | 6/1993 | McQuilkin et al. | | 5,474,557 A | 12/1995 | Mai |
| 5,222,971 A | 6/1993 | Willard et al. | | 5,474,572 A | 12/1995 | Hayhurst |
| 5,222,974 A | 6/1993 | Kensey et al. | | 5,476,505 A | 12/1995 | Limon |
| 5,226,908 A | 7/1993 | Yoon | | 5,478,352 A | 12/1995 | Fowler |
| 5,234,449 A | 8/1993 | Bruker et al. | | 5,478,353 A | 12/1995 | Yoon et al. |
| 5,236,435 A | 8/1993 | Sewell, Jr. | | 5,478,354 A | 12/1995 | Tovey et al. |
| 5,236,445 A | 8/1993 | Hayhurst et al. | | 5,486,195 A | 1/1996 | Myers et al. |
| 5,237,996 A | 8/1993 | Waldman | | 5,492,119 A | 2/1996 | Abrams |
| 5,242,457 A | 9/1993 | Akopov et al. | | 5,497,933 A | 3/1996 | DeFonzo et al. |
| 5,242,459 A | 9/1993 | Buelna | | 5,501,698 A | 3/1996 | Roth et al. |
| 5,246,156 A | 9/1993 | Rothfuss et al. | | 5,507,744 A | 4/1996 | Tay et al. |
| 5,246,443 A | 9/1993 | Mai | | 5,507,755 A | 4/1996 | Gresl et al. |
| 5,250,058 A * | 10/1993 | Miller et al. .................. 606/154 | | 5,514,159 A | 5/1996 | Matula et al. |
| 5,254,105 A | 10/1993 | Haaga | | 5,521,184 A | 5/1996 | Zimmermann |
| 5,258,015 A | 11/1993 | Li et al. | | 5,522,840 A | 6/1996 | Krajicek |
| 5,269,792 A | 12/1993 | Kovac et al. | | 5,527,322 A | 6/1996 | Klein et al. |
| 5,275,616 A | 1/1994 | Fowler | | 5,536,251 A | 7/1996 | Evard et al. |
| 5,281,422 A | 1/1994 | Badylak et al. | | 5,536,267 A | 7/1996 | Edwards |
| 5,282,808 A | 2/1994 | Kovac et al. | | 5,540,712 A | 7/1996 | Kleshinski et al. |
| 5,282,827 A | 2/1994 | Kensey et al. | | 5,540,716 A | 7/1996 | Hlavacek |
| 5,282,832 A | 2/1994 | Toso et al. | | 5,543,520 A | 8/1996 | Zimmermann |
| 5,289,963 A | 3/1994 | McGarry et al. | | 5,544,802 A | 8/1996 | Crainich |
| 5,290,243 A | 3/1994 | Chodorow et al. | | 5,547,474 A | 8/1996 | Kloeckl et al. |
| 5,290,310 A | 3/1994 | Makower et al. | | 5,560,532 A | 10/1996 | DeFonzo et al. |
| 5,292,309 A | 3/1994 | Van Tassel et al. | | 5,562,684 A | 10/1996 | Kammerer |
| 5,292,332 A | 3/1994 | Lee | | 5,571,120 A | 11/1996 | Yoon |
| 5,304,184 A | 4/1994 | Hathaway et al. | | 5,573,540 A | 11/1996 | Yoon |
| 5,304,204 A | 4/1994 | Bregen | | 5,573,784 A | 11/1996 | Badylak et al. |
| 5,306,254 A | 4/1994 | Nash et al. | | 5,575,771 A | 11/1996 | Walinsky |
| 5,306,280 A | 4/1994 | Bregen et al. | | 5,584,879 A | 12/1996 | Reimold et al. |
| 5,309,927 A | 5/1994 | Welch | | 5,591,205 A | 1/1997 | Fowler |
| 5,318,542 A | 6/1994 | Hirsch et al. | | 5,593,412 A | 1/1997 | Martinez |
| 5,320,639 A | 6/1994 | Rudnick | | 5,593,422 A | 1/1997 | Muijs Van de Moer et al. |
| 5,327,908 A | 7/1994 | Gerry | | 5,593,425 A | 1/1997 | Bonutti et al. |
| 5,330,442 A | 7/1994 | Green et al. | | 5,601,602 A | 2/1997 | Fowler |
| 5,330,445 A | 7/1994 | Haaga | | 5,609,597 A | 3/1997 | Lehrer |
| 5,334,216 A | 8/1994 | Vidal et al. | | 5,611,986 A | 3/1997 | Datta et al. |
| 5,334,217 A | 8/1994 | Das | | 5,613,974 A | 3/1997 | Andreas et al. |
| 5,335,680 A | 8/1994 | Moore | | 5,613,975 A | 3/1997 | Christy |
| 5,340,360 A | 8/1994 | Stefanchik | | 5,618,291 A | 4/1997 | Thompson et al. |
| 5,350,399 A | 9/1994 | Erlebacher et al. | | 5,618,306 A | 4/1997 | Roth et al. |
| 5,352,229 A | 10/1994 | Goble et al. | | 5,620,452 A | 4/1997 | Yoon |
| 5,354,279 A | 10/1994 | Hofling | | 5,620,461 A | 4/1997 | Muijs et al. |
| 5,364,406 A | 11/1994 | Sewell, Jr. | | 5,630,824 A | 5/1997 | Hart |
| 5,364,408 A | 11/1994 | Gordon | | 5,643,318 A | 7/1997 | Tsukernik et al. |
| 5,366,458 A | 11/1994 | Korthoff et al. | | 5,645,553 A | 7/1997 | Kolesa et al. |
| 5,366,479 A | 11/1994 | McGarry et al. | | 5,645,565 A | 7/1997 | Rudd et al. |
| 5,376,101 A | 12/1994 | Green et al. | | 5,645,566 A | 7/1997 | Brenneman et al. |
| 5,383,896 A | 1/1995 | Gershony et al. | | 5,645,567 A | 7/1997 | Crainich |
| 5,383,905 A | 1/1995 | Golds et al. | | 5,647,372 A | 7/1997 | Tovey et al. |
| RE34,866 E | 2/1995 | Kensey et al. | | 5,649,959 A | 7/1997 | Hannam et al. |
| 5,391,173 A | 2/1995 | Wilk | | D383,539 S | 9/1997 | Croley |
| 5,392,978 A | 2/1995 | Velez et al. | | 5,669,917 A | 9/1997 | Sauer et al. |
| 5,395,030 A | 3/1995 | Kuramoto et al. | | 5,672,174 A | 9/1997 | Gough et al. |
| 5,403,330 A | 4/1995 | Tuason | | 5,674,231 A | 10/1997 | Green et al. |

| Patent | Date | Inventor |
|---|---|---|
| 5,676,689 A | 10/1997 | Kensey et al. |
| 5,676,974 A | 10/1997 | Valdes et al. |
| 5,681,334 A | 10/1997 | Evans et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,709,708 A | 1/1998 | Thal |
| 5,713,899 A | 2/1998 | Marnay et al. |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A * | 3/1998 | Van Tassel et al. ........... 606/213 |
| 5,728,143 A | 3/1998 | Gough et al. |
| 5,732,872 A | 3/1998 | Bolduc et al. |
| 5,735,873 A | 4/1998 | MacLean |
| 5,735,875 A | 4/1998 | Bonutti et al. |
| 5,735,877 A | 4/1998 | Pagedas |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,759,189 A | 6/1998 | Ferragamo et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,150 A | 7/1998 | Nolan et al. |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,951,518 A | 9/1999 | Licata et al. |
| 5,951,547 A | 9/1999 | Gough et al. |
| 5,951,576 A | 9/1999 | Wakabayashi |
| 5,951,589 A | 9/1999 | Epstein et al. |
| 5,957,936 A | 9/1999 | Yoon et al. |
| 5,957,938 A | 9/1999 | Zhu et al. |
| 5,964,782 A | 10/1999 | LaFontaine et al. |
| 5,976,159 A | 11/1999 | Bolduc et al. |
| 5,976,161 A | 11/1999 | Kirsch et al. |
| 5,980,517 A | 11/1999 | Gough et al. |
| 5,984,934 A | 11/1999 | Ashby et al. |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,071,300 A | 6/2000 | Brenneman et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,099,553 A | 8/2000 | Hart et al. |
| 6,102,271 A * | 8/2000 | Longo et al. ................ 227/180.1 |
| 6,106,545 A | 8/2000 | Egan |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,120,524 A | 9/2000 | Taheri |
| 6,126,675 A | 10/2000 | Shchervinsky et al. |
| 6,126,677 A | 10/2000 | Ganaja et al. |

| | | |
|---|---|---|
| 6,136,010 A | 10/2000 | Modesitt et al. |
| 6,143,004 A | 11/2000 | Davis |
| 6,143,017 A | 11/2000 | Thal |
| 6,149,660 A | 11/2000 | Laufer et al. |
| 6,149,667 A * | 11/2000 | Hovland et al. ............... 606/219 |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,324 B1 | 1/2001 | Egan et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,203,565 B1 | 3/2001 | Bonutti et al. |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,592 B1 | 5/2001 | Bonutti et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 * | 9/2001 | Zhu et al. ...................... 606/213 |
| 6,296,657 B1 | 10/2001 | Brucker |
| 6,305,891 B1 | 10/2001 | Burlingame |
| 6,306,081 B1 | 10/2001 | Ishikawa et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,780,197 B2 | 2/2002 | Carley et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,517,498 B1 | 2/2003 | Burbank et al. |
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,623,509 B2 | 9/2003 | Ginn |
| 6,623,510 B2 | 9/2003 | Carley et al. |
| 6,626,918 B1 | 9/2003 | Ginn et al. |
| 6,632,238 B1 | 10/2003 | Ginn et al. |
| 6,634,537 B2 | 10/2003 | Chen |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,051 B2 | 2/2004 | Nakada et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 | 8/2005 | Coleman et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,083,635 B2 | 8/2006 | Ginn |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,163,551 B2 | 1/2007 | Anthony et al. |

| | | | | | |
|---|---|---|---|---|---|
| 7,169,158 B2 | 1/2007 | Sniffin et al. | 2004/0158127 A1 | 8/2004 | Okada |
| 7,169,164 B2 | 1/2007 | Borillo et al. | 2004/0158287 A1 | 8/2004 | Cragg et al. |
| 7,211,101 B2 | 5/2007 | Carley et | 2004/0158309 A1 | 8/2004 | Wachter et al. |
| 7,270,672 B1 | 9/2007 | Singer | 2004/0167511 A1 | 8/2004 | Buehlmann et al. |
| 7,311,720 B2 | 12/2007 | Mueller et al. | 2004/0167570 A1 | 8/2004 | Pantages |
| 7,316,704 B2 | 1/2008 | Bagaoisan et al. | 2004/0191277 A1 | 9/2004 | Sawhney et al. |
| 7,326,230 B2 | 2/2008 | Ravikumar | 2004/0215232 A1 | 10/2004 | Belhe et al. |
| 7,331,979 B2 | 2/2008 | Khosravi et al. | 2004/0249412 A1 | 12/2004 | Snow et al. |
| 7,335,220 B2 | 2/2008 | Khosravi et al. | 2004/0254591 A1 | 12/2004 | Kanner et al. |
| D566,272 S | 4/2008 | Walberg et al. | 2004/0267193 A1 | 12/2004 | Bagaoisan et al. |
| 7,361,183 B2 | 4/2008 | Ginn | 2004/0267308 A1 | 12/2004 | Bagaoisan et al. |
| 7,361,185 B2 | 4/2008 | O'Malley et al. | 2004/0267312 A1 | 12/2004 | Kanner et al. |
| 7,393,363 B2 | 7/2008 | Ginn | 2005/0038460 A1 | 2/2005 | Jayaraman |
| 7,396,359 B1 * | 7/2008 | Derowe et al. ............ 606/213 | 2005/0038500 A1 | 2/2005 | Boylan et al. |
| 7,431,727 B2 | 10/2008 | Cole et al. | 2005/0059982 A1 | 3/2005 | Zung et al. |
| 7,507,200 B2 | 3/2009 | Okada | 2005/0075665 A1 | 4/2005 | Brenzel et al. |
| 7,533,790 B1 | 5/2009 | Knodel et al. | 2005/0085851 A1 | 4/2005 | Fiehler et al. |
| 7,597,706 B2 | 10/2009 | Kanner et al. | 2005/0085854 A1 | 4/2005 | Ginn |
| D611,144 S | 3/2010 | Reynolds | 2005/0085855 A1 | 4/2005 | Forsberg |
| 7,727,249 B2 | 6/2010 | Rahmani | 2005/0090859 A1 | 4/2005 | Ravlkumar |
| 7,731,655 B2 | 6/2010 | Smith et al. | 2005/0119695 A1 | 6/2005 | Carley et al. |
| 7,749,249 B2 | 7/2010 | Gelbart et al. | 2005/0121042 A1 | 6/2005 | Belhe et al. |
| 7,819,895 B2 | 10/2010 | Ginn et al. | 2005/0149117 A1 | 7/2005 | Khosravi et al. |
| 2001/0007077 A1 | 7/2001 | Ginn et al. | 2005/0165357 A1 | 7/2005 | McGuckin et al. |
| 2001/0031972 A1 | 10/2001 | Robertson et al. | 2005/0177189 A1 | 8/2005 | Ginn et al. |
| 2001/0046518 A1 | 11/2001 | Sawhney | 2005/0187564 A1 | 8/2005 | Jayaraman |
| 2001/0047180 A1 | 11/2001 | Grudem et al. | 2005/0216057 A1 | 9/2005 | Coleman et al. |
| 2001/0053909 A1 | 12/2001 | Nakada et al. | 2005/0222614 A1 | 10/2005 | Ginn et al. |
| 2002/0026208 A1 | 2/2002 | Belef | 2005/0234508 A1 | 10/2005 | Cummins et al. |
| 2002/0026215 A1 | 2/2002 | Redmond et al. | 2005/0245876 A1 | 11/2005 | Khosravi et al. |
| 2002/0038127 A1 | 3/2002 | Blatter et al. | 2005/0267528 A1 | 12/2005 | Ginn et al. |
| 2002/0042622 A1 | 4/2002 | Vargas et al. | 2005/0267530 A1 | 12/2005 | Cummins et al. |
| 2002/0049472 A1 | 4/2002 | Coleman et al. | 2005/0273136 A1 | 12/2005 | Belef et al. |
| 2002/0058960 A1 | 5/2002 | Hudson et al. | 2005/0273137 A1 | 12/2005 | Ginn |
| 2002/0072768 A1 | 6/2002 | Ginn | 2005/0274768 A1 | 12/2005 | Cummins et al. |
| 2002/0077657 A1 | 6/2002 | Ginn et al. | 2005/0283188 A1 | 12/2005 | Loshakove et al. |
| 2002/0082641 A1 | 6/2002 | Ginn et al. | 2006/0020270 A1 | 1/2006 | Jabba et al. |
| 2002/0099389 A1 | 7/2002 | Michler et al. | 2006/0030867 A1 | 2/2006 | Zadno |
| 2002/0106409 A1 | 8/2002 | Sawhney et al. | 2006/0034930 A1 | 2/2006 | Khosravi et al. |
| 2002/0107542 A1 | 8/2002 | Kanner et al. | 2006/0047313 A1 | 3/2006 | Khanna et al. |
| 2002/0151921 A1 | 10/2002 | Kanner et al. | 2006/0089635 A1 | 4/2006 | Young et al. |
| 2002/0183786 A1 | 12/2002 | Girton | 2006/0095029 A1 | 5/2006 | Young et al. |
| 2002/0188275 A1 | 12/2002 | McGuckin et al. | 2006/0100664 A1 | 5/2006 | Pai et al. |
| 2002/0193808 A1 | 12/2002 | Belef et al. | 2006/0135989 A1 | 6/2006 | Carley et al. |
| 2003/0004543 A1 | 1/2003 | Gleeson et al. | 2006/0144479 A1 | 7/2006 | Carley et al. |
| 2003/0009180 A1 | 1/2003 | Hinchliffe et al. | 2006/0167484 A1 | 7/2006 | Carley et al. |
| 2003/0009196 A1 | 1/2003 | Peterson | 2006/0190014 A1 | 8/2006 | Ginn et al. |
| 2003/0032981 A1 | 2/2003 | Kanner et al. | 2006/0190037 A1 | 8/2006 | Carley et al. |
| 2003/0045893 A1 | 3/2003 | Ginn | 2006/0190038 A1 | 8/2006 | Carley et al. |
| 2003/0055455 A1 | 3/2003 | Yang et al. | 2006/0195123 A1 | 8/2006 | Ginn et al. |
| 2003/0065358 A1 | 4/2003 | Frecker et al. | 2006/0195124 A1 | 8/2006 | Ginn et al. |
| 2003/0078598 A1 | 4/2003 | Ginn et al. | 2006/0206146 A1 | 9/2006 | Tenerz |
| 2003/0083679 A1 | 5/2003 | Grudem et al. | 2006/0253037 A1 | 11/2006 | Ginn et al. |
| 2003/0093096 A1 | 5/2003 | McGuckin et al. | 2006/0253072 A1 | 11/2006 | Pai et al. |
| 2003/0097140 A1 | 5/2003 | Kanner | 2006/0259049 A1 | 11/2006 | Harada et al. |
| 2003/0109890 A1 | 6/2003 | Kanner et al. | 2006/0265012 A1 | 11/2006 | Anderson |
| 2003/0125766 A1 | 7/2003 | Ding | 2006/0287674 A1 | 12/2006 | Ginn et al. |
| 2003/0158577 A1 | 8/2003 | Pantages et al. | 2007/0010853 A1 | 1/2007 | Ginn et al. |
| 2003/0158578 A1 | 8/2003 | Pantages et al. | 2007/0010854 A1 | 1/2007 | Cummins et al. |
| 2003/0195504 A1 | 10/2003 | Tallarida et al. | 2007/0021778 A1 | 1/2007 | Carly |
| 2003/0195561 A1 | 10/2003 | Carley et al. | 2007/0049967 A1 | 3/2007 | Sibbitt, Jr. et al. |
| 2003/0233095 A1 | 12/2003 | Urbanski et al. | 2007/0049968 A1 | 3/2007 | Sibbitt, Jr. et al. |
| 2004/0009205 A1 | 1/2004 | Sawhney | 2007/0060895 A1 | 3/2007 | Sibbitt, Jr. et al. |
| 2004/0009289 A1 | 1/2004 | Carley et al. | 2007/0060950 A1 | 3/2007 | Khosravi et al. |
| 2004/0010285 A1 | 1/2004 | Carley et al. | 2007/0083230 A1 | 4/2007 | Javois |
| 2004/0039414 A1 | 2/2004 | Carley et al. | 2007/0112304 A1 | 5/2007 | Voss |
| 2004/0068273 A1 | 4/2004 | Fariss et al. | 2007/0123817 A1 | 5/2007 | Khosravi et al. |
| 2004/0073236 A1 | 4/2004 | Carley et al. | 2007/0179527 A1 | 8/2007 | Eskuri et al. |
| 2004/0073255 A1 | 4/2004 | Ginn et al. | 2007/0203506 A1 | 8/2007 | Sibbitt, Jr. et al. |
| 2004/0082906 A1 | 4/2004 | Tallarida et al. | 2007/0203507 A1 | 8/2007 | McLaughlin et al. |
| 2004/0087985 A1 | 5/2004 | Loshakove et al. | 2007/0225755 A1 | 9/2007 | Preinitz et al. |
| 2004/0092964 A1 | 5/2004 | Modesitt et al. | 2007/0225756 A1 | 9/2007 | Preinitz et al. |
| 2004/0092968 A1 | 5/2004 | Caro et al. | 2007/0225757 A1 | 9/2007 | Preinitz et al. |
| 2004/0093027 A1 | 5/2004 | Fabisiak et al. | 2007/0225758 A1 | 9/2007 | Preinitz et al. |
| 2004/0097978 A1 | 5/2004 | Modesitt et al. | 2007/0239209 A1 | 10/2007 | Fallman |
| 2004/0127940 A1 | 7/2004 | Ginn et al. | 2007/0250080 A1 | 10/2007 | Jones et al. |
| 2004/0143290 A1 | 7/2004 | Brightbill | 2007/0265658 A1 | 11/2007 | Nelson et al. |
| 2004/0153122 A1 | 8/2004 | Palermo | 2007/0276488 A1 | 11/2007 | Wachter et al. |
| 2004/0153123 A1 | 8/2004 | Palermo et al. | 2008/0004636 A1 | 1/2008 | Walberg et al. |

| | | | | | | |
|---|---|---|---|---|---|---|
| 2008/0004640 | A1 | 1/2008 | Ellingwood | SU | 1405828 | 6/1988 |
| 2008/0009794 | A1 | 1/2008 | Bagaoisan et al. | SU | 1456109 | 2/1989 |
| 2008/0045979 | A1 | 2/2008 | Ma | SU | 1560133 | 4/1990 |
| 2008/0058839 | A1 | 3/2008 | Nobles et al. | WO | WO 95/21573 | 8/1995 |
| 2008/0065151 | A1 | 3/2008 | Ginn | WO | WO 96/24291 | 8/1996 |
| 2008/0065152 | A1 | 3/2008 | Carley | WO | WO 97/07741 | 3/1997 |
| 2008/0086075 | A1 | 4/2008 | Isik et al. | WO | WO97/20505 | 6/1997 |
| 2008/0093414 | A1 | 4/2008 | Bender et al. | WO | WO 97/27897 | 8/1997 |
| 2008/0114395 | A1 | 5/2008 | Mathisen et al. | WO | WO 97/28745 | 8/1997 |
| 2008/0221616 | A1 | 9/2008 | Ginn et al. | WO | WO 98/06346 | 2/1998 |
| 2008/0287967 | A1 | 11/2008 | Andreas et al. | WO | WO 98/06448 | 2/1998 |
| 2008/0300628 | A1 | 12/2008 | Ellingwood | WO | WO 98/16161 | 4/1998 |
| 2008/0312686 | A1 | 12/2008 | Ellingwood | WO | WO 98/17179 | 4/1998 |
| 2008/0312740 | A1 | 12/2008 | Wachter et al. | WO | WO 98/18389 | 5/1998 |
| 2008/0319475 | A1 | 12/2008 | Clark | WO | WO98/24374 | 6/1998 |
| 2009/0157101 | A1 | 6/2009 | Reyes et al. | WO | WO 98/25508 | 6/1998 |
| 2009/0157102 | A1 | 6/2009 | Reynolds et al. | WO | WO 98/58591 | 12/1998 |
| 2009/0157103 | A1 | 6/2009 | Walberg et al. | WO | WO 99/21491 | 5/1999 |
| 2009/0187215 | A1 | 7/2009 | Mackiewicz et al. | WO | WO 99/40849 | 8/1999 |
| 2009/0254119 | A1 | 10/2009 | Sibbitt, Jr. et al. | WO | WO 99/60941 | 12/1999 |
| 2009/0287244 | A1 | 11/2009 | Kokish | WO | WO99/62408 | 12/1999 |
| 2010/0114156 | A1 | 5/2010 | Mehl | WO | WO 99/62415 | 12/1999 |
| 2010/0114159 | A1 | 5/2010 | Roorda et al. | WO | WO 00/06029 | 2/2000 |
| 2010/0130965 | A1 | 5/2010 | Sibbitt, Jr. | WO | WO 00/07505 | 2/2000 |
| 2010/0168790 | A1 | 7/2010 | Clark | WO | WO 00/07640 | 2/2000 |
| 2010/0179567 | A1 | 7/2010 | Voss et al. | WO | WO 00/27311 | 5/2000 |
| 2010/0179571 | A1 | 7/2010 | Voss | WO | WO 00/27313 | 5/2000 |
| 2010/0179572 | A1 | 7/2010 | Voss et al. | WO | WO 00/56223 | 9/2000 |
| 2010/0179589 | A1 | 7/2010 | Roorda et al. | WO | WO 00/56227 | 9/2000 |
| 2010/0179590 | A1 | 7/2010 | Fortson et al. | WO | WO 00/56228 | 9/2000 |
| 2010/0185234 | A1 | 7/2010 | Fortson et al. | WO | WO 00/71032 | 11/2000 |
| | | | | WO | WO 01/21058 | 3/2001 |

FOREIGN PATENT DOCUMENTS

| | | | | | |
|---|---|---|---|---|---|
| CA | 2 339 060 | 2/2000 | WO | WO 01/35832 | 5/2001 |
| DE | 197 11 288 | 1/1998 | WO | WO 01/47594 | 7/2001 |
| DE | 297 23 736 U 1 | 4/1999 | WO | WO 01/49186 | 7/2001 |
| DE | 19859952 | 2/2000 | WO | WO 01/91628 | 12/2001 |
| DE | 102006056283 | 6/2008 | WO | WO 02/19915 | 3/2002 |
| EP | 0 386 361 | 9/1990 | WO | WO 02/19920 | 3/2002 |
| EP | 0 534 696 | 3/1993 | WO | WO 02/19922 | 3/2002 |
| EP | 0 756 851 | 2/1997 | WO | WO 02/19924 | 3/2002 |
| EP | 0 774 237 | 5/1997 | WO | WO 02/28286 | 4/2002 |
| EP | 0 858 776 | 8/1998 | WO | WO 02/38055 | 5/2002 |
| EP | 0 941 697 | 9/1999 | WO | WO 02/45593 | 6/2002 |
| EP | 1 867 287 | 12/2007 | WO | WO 02/45594 | 6/2002 |
| FR | 2 443 238 | 7/1980 | WO | WO 02/062234 | 8/2002 |
| FR | 2 715 290 | 7/1995 | WO | WO 02/98302 | 12/2002 |
| FR | 2 722 975 | 2/1996 | WO | WO 03/013363 | 2/2003 |
| FR | 2 768 324 | 3/1999 | WO | WO 03/013364 | 2/2003 |
| GB | 1 358 466 | 7/1974 | WO | WO 03/047434 | 6/2003 |
| GB | 2 075 144 | 11/1981 | WO | WO 03/071955 | 9/2003 |
| GB | 2 397 240 | 7/2004 | WO | WO 03/071956 | 9/2003 |
| IE | S 2000/0722 | 10/2001 | WO | WO 03/094748 | 11/2003 |
| IE | S 2000/0724 | 10/2001 | WO | WO 03/101310 | 12/2003 |
| IE | S 2001/0547 | 7/2002 | WO | WO 03/071957 | 1/2004 |
| IE | S 2001/0815 | 7/2002 | WO | WO 2004/004578 | 1/2004 |
| IE | S 2001/0748 | 8/2002 | WO | WO 2004/012602 | 2/2004 |
| IE | S 2001/0749 | 8/2002 | WO | WO 2004/060169 | 7/2004 |
| IE | S 2002/0452 | 12/2002 | WO | WO 2004/069054 | 8/2004 |
| IE | S 2002/0664 | 2/2003 | WO | WO 2005/000126 | 1/2005 |
| IE | S 2002/0665 | 2/2003 | WO | WO 2005/006990 | 1/2005 |
| IE | S 2002/0451 | 7/2003 | WO | WO 2005/041782 | 5/2005 |
| IE | S 2002/0552 | 7/2003 | WO | WO 2005/063129 | 7/2005 |
| IE | S 2003/0424 | 12/2003 | WO | WO 2005/082256 | 9/2005 |
| IE | S 2003/0490 | 1/2004 | WO | WO 2005/092204 | 10/2005 |
| IE | S 2004/0368 | 11/2005 | WO | WO 2005/110240 | 11/2005 |
| IE | S 2005/0342 | 11/2005 | WO | WO 2005/112782 | 12/2005 |
| JP | 58-181006 | 12/1983 | WO | WO 2005/115251 | 12/2005 |
| JP | 12 74750 | 11/1989 | WO | WO 2005/115521 | 12/2005 |
| JP | 11500642 | 8/1997 | WO | WO 2006/000514 | 1/2006 |
| JP | 2000102546 | 4/2000 | WO | WO 2006/026116 | 3/2006 |
| NL | 9302140 | 7/1995 | WO | WO 2006/052611 | 5/2006 |
| PL | 171425 | 4/1997 | WO | WO 2006/052612 | 5/2006 |
| RU | 2086192 | 8/1997 | WO | WO 2006/078578 | 7/2006 |
| SU | 197801 | 6/1967 | WO | WO 2006/083889 | 8/2006 |
| SU | 495067 | 12/1975 | WO | WO 2006/115901 | 11/2006 |
| SU | 912155 | 3/1982 | WO | WO 2006/115904 | 11/2006 |
| SU | 1243708 | 7/1986 | WO | WO 2006/118877 | 11/2006 |
| SU | 1324650 | 7/1987 | WO | WO 2007/005585 | 1/2007 |
| | | | WO | WO 2007/025014 | 3/2007 |

| | | |
|---|---|---|
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/036384 | 3/2008 |
| WO | WO 2008/074027 | 6/2008 |
| WO | WO 2008/031102 | 9/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, Mail Date Aug. 27, 2004.
2002/0072768, Office Action, Mail Date Feb. 23, 2005.
2002/0072768, Office Action, Mail Date Apr. 11, 2005.
2002/0072768, Office Action, Mail Date Jul. 27, 2005.
2002/0072768, Office Action, Mail Date Mar. 6, 2006.
2002/0072768, Office Action, Mail Date May 24, 2006.
2002/0072768, Office Action, Mail Date Oct. 26, 2006.
2002/0072768, Office Action, Mail Date Apr. 19, 2007.
2003/0078598, Office Action, Mail Date Feb. 9, 2005.
2003/0078598, Office Action, Mail Date May 26, 2005.
2003/0078598, Office Action, Mail Date Oct. 4, 2005.
2003/0078598, Notice of Allowance, Mail Date May 10, 2006.
2003/0078598, Notice of Allowance, Mail Date Jul. 2, 2007.
2003/0195561, Office Action, Mail Date Jun. 10, 2004.
2003/0195561, Notice of Allowance, Mail Date Sep. 21, 2004.
2003/0195561, Office Action, Mail Date Jan. 3, 2006.
2003/0195561, Issue Notification, Mail Date Feb. 15, 2006.
2003/0195561, Office Action, Mail Date May 16, 2006.
2003/0195561, Notice of Allowance, Mail Date Dec. 28, 2006.
2003/0195561, Notice of Allowance, Mail Date Jul. 10, 2007.
2003/0195561, Notice of Allowance, Mail Date Aug. 2, 2007.
2004/0153123, Office Action, Mail Date Sep. 22, 2006.
2004/0153123, Office Action, Mail Date Jan. 31, 2007.
2004/0153123, Office Action, Mail Date Sep. 18, 2007.
2004/0153122, Office Action, Mail Date Nov. 30, 2005.
2004/0153122, Office Action, Mail Date Aug. 23, 2006.
2004/0153122, Office Action, Mail Date Feb. 13, 2007.
2004/0153122, Office Action, Mail Date Sep. 12, 2007.
2004/0073255, Office Action, Mail Date Sep. 15, 2006.
2004/0073255, Office Action, Mail Date Apr. 18, 2007.
2004/0073236, Office Action, Mail Date Sep. 19, 2006.
2004/0073236, Office Action, Mail Date May 2, 2007.
2004/0009289, Office Action, Mail Date Jun. 30, 2006.
2004/0009289, Office Action, Mail Date Oct. 20, 2006.
2004/0009289, Office Action, Mail Date May 29, 2007.
2004/0167570, Office Action, Mail Date Oct. 30, 2006.
2004/0167570, Office Action, Mail Date Apr. 17, 2007.
2004/0167570, Office Action, Mail Date Aug. 31, 2007.
2005/0274768, Office Action, Mail Date Oct. 19, 2006.
2005/0274768, Office Action, Mail Date Aug. 10, 2007.
2005/0216057, Office Action, Mail Date Feb. 6, 2007.
2005/0216057, Office Action, Mail Date May 30, 2007.
2005/0234508, Office Action, Mail Date Aug. 13, 2007.
2006/0135989, Office Action, Mail Date Nov. 30, 2006.
2006/0135989, Office Action, Mail Date Sep. 5, 2007.
2006/0195124, Office Action, Mail Date Jun. 6, 2007.
2006/0195123, Office Action, Mail Date May 14, 2007.
6,197,042, Notice of Allowance, Mail Date Nov. 6, 2000.
6,197,042, Issue Notification, Mail Date Feb. 15, 2001.
6,277,140, Office Action, Mail Date Mar. 26, 2001.
6,277,140, Notice of Allowance, Mail Date Jun. 4, 2001.
6,277,140, Issue Notification, Mail Date Aug. 6, 2001.
6,391,048, Notice of Allowance, Mail Date Mar. 26, 2001.
6,391,048, Office Action, Mail Date Sep. 5, 2001.
6,391,048, Notice of Allowance, Mail Date Feb. 11, 2002.
6,391,048, Issue Notification, Mail Date May 3, 2002.
6,461,364, Notice of Allowance, Mail Date May 6, 2002.
6,461,364, Issue Notification, Mail Date Sep. 19, 2002.
6,582,452, Notice of Allowance, Mail Date Jan. 31, 2003.
6,582,452, Issue Notification, Mail Date Jun. 5, 2003.
6,616,686, Office Action, Mail Date Dec. 17, 2002.
6,616,686, Notice of Allowance, Mail Date Apr. 21, 2003.
6,616,686, Issue Notification, Mail Date Aug. 21, 2003.
6,623,510, Notice of Allowance, Mail Date Apr. 11, 2003.
6,623,510, Office Action, Mail Date Jun. 9, 2003.
6,623,510, Issue Notification, Mail Date Sep. 4, 2003.
6,632,238, Office Action, Mail Date Feb. 26, 2003.
6,632,238, Notice of Allowance, Mail Date Jun. 16, 2003.
6,632,238, Issue Notification, Mail Date Sep. 25, 2003.
6,669,714, Office Action, Mail Date Mar. 4, 2003.
6,669,714, Notice of Allowance, Mail Date Jul. 28, 2003.
6,669,714, Issue Notification, Mail Date Dec. 11, 2003.
6,695,867, Notice of Allowance, Mail Date Sep. 29, 2003.
6,695,867, Issue Notification, Mail Date Feb. 5, 2004.
6,719,777, Office Action, Mail Date Feb. 20, 1987.
6,719,777, Notice of Allowance, Mail Date Jul. 24, 1987.
6,719,777, Issue Notification, Mail Date Mar. 25, 2004.
6,749,621, Notice of Allowance, Mail Date Feb. 9, 2004.
6,749,621, Office Action, Mail Date Apr. 13, 2004.
6,749,621, Issue Notification, Mail Date May 27, 2004.
6,780,197, Office Action, Mail Date Sep. 11, 2003.
6,780,197, Office Action, Mail Date Feb. 9, 2004.
6,780,197, Notice of Allowance, Mail Date Mar. 17, 2004.
6,780,197, Issue Notification, Mail Date Aug. 5, 2004.
6,926,731, Office Action, Mail Date Nov. 16, 2004.
6,926,731, Notice of Allowance, Mail Date Apr. 6, 2005.
6,926,731, Issue Notification, Mail Date Jul. 20, 2005.
6,942,674, Office Action, Mail Date Sep. 29, 2004.
6,942,674, Notice of Allowance, Mail Date May 13, 2005.
6,942,674, Issue Notification, Mail Date Aug. 24, 2005.
7,001,398, Office Action, Mail Date Mar. 22, 2005.
7,001,398, Notice of Allowance, Mail Date Jul. 6, 2005.
7,001,398, Notice of Allowance, Mail Date Oct. 5, 2005.
7,001,398, Issue Notification, Mail Date Feb. 21, 2006.
7,008,435, Office Action, Mail Date Apr. 20, 2005.
7,008,435, Office Action, Mail Date Aug. 10, 2005.
7,008,435, Notice of Allowance, Mail Date Oct. 18, 2005.
7,008,435, Issue Notification, Mail Date Feb. 15, 2006.
7,108,709, Office Action, Mail Date Jul. 27, 2004.
7,108,709, Office Action, Mail Date Dec. 17, 2004.
7,108,709, Notice of Allowance, Mail Date Mar. 9, 2005.
7,108,709, Office Action, Mail Date Aug. 11, 2006.
7,108,709, Issue Notification, Mail Date Aug. 30, 2006.
7,111,768, Office Action, Mail Date Feb. 23, 2006.
7,111,768, Notice of Allowance, Mail Date May 31, 2006.
7,111,768, Issue Notification, Mail Date Sep. 6, 2006.
7,163,551, Office Action, Mail Date Jan. 10, 2006.
7,163,551, Notice of Allowance, Mail Date Sep. 20, 2006.
7,163,551, Issue Notification, Mail Date Dec. 27, 2006.
7,211,101, Office Action, Mail Date Aug. 10, 2005.
7,211,101, Office Action, Mail Date Dec. 19, 2005.
7,211,101, Office Action, Mail Date Apr. 21, 2006.
7,211,101, Notice of Allowance, Mail Date Dec. 27, 2006.
7,211,101, Issue Notification, Mail Date Apr. 11, 2007.
U.S. Appl. No. 10/541,083, Office Action, Mail Date Oct. 16, 2007.
"Hand tool for forming telephone connections—comprises pliers with reciprocably driven ram crimping clip around conductors against anvil". Derwent-ACC-No: 1978-B8090A.
U.S. Appl. No. 10/356,214, filed Mar. 6, 2008, Office Action.
U.S. Appl. No. 10/435,104, filed Apr. 4, 2008, Notice of Allowance.
U.S. Appl. No. 10/787,073, filed Feb. 22, 2008, Office Action.
U.S. Appl. No. 11/113,549, filed Apr. 16, 2008, Office Action.
U.S. Appl. No. 10/682,459, filed Apr. 2, 2008, Office Action.

U.S. Appl. No. 10/786,444, filed Feb. 24, 2004, Office Action.
U.S. Appl. No. 10/638,115, filed Feb. 7, 2008, Office Action.
U.S. Appl. No. 10/264,306, filed Feb. 4, 2008, Notice of Allowance.
U.S. Appl. No. 11/411,925, filed Feb. 5, 2008, Office Action.
U.S. Appl. No. 10/517,004, filed Jan. 30, 2008, Office Action.
U.S. Appl. No. 10/006,400, Mail Date Apr. 2, 2008, Office Action.
U.S. Appl. No. 10/541,083, Mail Date May 5, 2008, Office Action.
U.S. Appl. No. 10/667,144, Mail Date May 12, 2008, Office Action.
U.S. Appl. No. 11/152,562, Mail Date May 13, 2008, Office Action.
U.S. Appl. No. 11/344,891, Mail Date Apr. 29, 2008, Office Action.
U.S. Appl. No. 11/406,203, Mail Date May 23, 2008, Notice of Allowance.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Childrens's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H DE Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, Vol. 178, No. 3, Department of Surgery, Section of Vascular Surgery, Ochsner Medical Institutions, New Orleans, La.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino Et Al, a Randomized Study of the 8 French Hemostatic Puncture Colosure Device vs Manual Compression After Coronary Interventions, Journal of the American College of Cardiology, Feb. 1995, p. 262A, vol. 25.—No. 2, Supplement 1.
Swee Lian Tan, MD, PhD, FACS, Explanation of Infected Hemostatic Puncture Closure Devices—A Case Report, Vascular and Endocascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel and Skin Staples: Description of the Technique and Case Reports, Annals of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
Ut Aker et al, Immediate arterial hemostasis after cardiac catheterization: initial experience with a new punture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts:Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 10/264,306, Mail Date Jun. 27, 2008, Office Action.
U.S. Appl. No. 10/435,104, Mail Date Sep. 26, 2008, Notice Of Allowance.
U.S. Appl. No. 10/541,083, Mail Date Sep. 19, 2008, Notice Of Allowance.
U.S. Appl. No. 10/616,832, Mail Date Sep. 17, 2008, Office Action.
U.S. Appl. No. 10/786,444, Mail Date Oct. 17, 2008, Office Action.
U.S. Appl. No. 11/198,811, Mail Date Aug. 26, 2008, Office Action.

U.S. Appl. No. 11/406,203, Mail Date Sep. 22, 2008, Notice Of Allowance.
U.S. Appl. No. 60/696,069, filed Jul. 1, 2005, Pantages et al.
U.S. Appl. No. 60/946026, filed Jun. 25, 2007, Ellingwood.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
McCarthy, et al., "Tension (Stay) Suture Bridge", J. of International College of Surgeons, 34(5), pp. 613-614 (Nov. 1960). cited by other.
U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Acton.
U.S. Appl. No. 09/680,837, Mail Date Jun. 16, 2003, Notice of Allowance.
U.S. Appl. No. 09/680,837, Mail Date Sep. 11, 2003, Issue Notification.
U.S. Appl. No. 10/006,400, Mail Date Jan. 2, 2009, Office Action.
U.S. Appl. No. 10/006,400, Mail Date Jul. 9, 2009, Notice of Allowance.
U.S. Appl. No. 10/027,681, Mail Date Jul. 8, 2009, Office Action.
U.S. Appl. No. 10/264,306, Mail Date Feb. 26, 2009, Office Action.
U.S. Appl. No. 10/305,923, Mail Date Nov. 1, 2004, Office Action.
U.S. Appl. No. 10/305,923, Mail Date Mar. 3, 2005, Notice of Allowance.
U.S. Appl. No. 10/356,214, Mail Date Nov. 2, 2008, Office Action.
U.S. Appl. No. 10/356,214, Mail Date Apr. 29, 2009, Office Action.
U.S. Appl. No. 10/435,104, Mail Date Nov. 14, 2007, Notice of Allowance.
U.S. Appl. No. 10/435,104, Mail Date Dec. 22, 2008, Notice of Allowance.
U.S. Appl. No. 10/517,004, Mail Date Aug. 13, 2008, Notice of Allowance.
U.S. Appl. No. 10/517004, Mail Date Feb. 10, 2009, Notice of Allowance.
U.S. Appl. No. 10/517,004, Mail Date Jun. 26, 2009, Notice of Allowance.
U.S. Appl. No. 10/541,083, Mail Date Oct. 31, 2007, Office Action.
U.S. Appl. No. 10/541,083, Mail Date Dec. 29, 2008, Notice of Allowance.
U.S. Appl. No. 10/541,083, Mail Date Apr. 16, 2009, Notice of Allowance.
U.S. Appl. No. 10/638,115, Mail Date Oct. 29, 2008, Office Action.
U.S. Appl. No. 10/638,115, Mail Date May 7, 2009, Notice of Allowance.
U.S. Appl. No. 10/667,144, Mail Date Mar. 24, 2009, Office Action.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/669,313, Mail Date Nov. 15, 2006, Issue Notification.
U.S. Appl. No. 10/682,459, Mail Date Dec. 4, 2008, Office Action.
U.S. Appl. No. 10/682,459, Mail Date Jun. 10, 2009, Office Action.
U.S. Appl. No. 10/786,444, Mail Date Jun. 18, 2009, Office Action.
U.S. Appl. No. 10/787,073, Mail Date Nov. 12, 2008, Office Action.
U.S. Appl. No. 10/908,721, Mail Date Nov. 25, 2008, Office Action.
U.S. Appl. No. 10/908,721, Mail Date Jun. 23, 2009, Office Action.
U.S. Appl. No. 11/048,503, Mail Date Mar. 13, 2009, Office Action.
U.S. Appl. No. 11/048,503, Mail Date Jun. 26, 2009, Office Action.
U.S. Appl. No. 11/152,562, Mail Date Feb. 13, 2009, Office Action.
U.S. Appl. No. 11/152,562, Mail Date Jul. 6, 2009, Office Action.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/344,891, Mail Date Dec. 8, 2008, Office Action.
U.S. Appl. No. 11/344,891, Mail Date Feb. 26, 2009, Office Action.
U.S. Appl. No. 11/390,586, Mail Date Jun. 24, 2009, Office Action.
U.S. Appl. No. 11/396,141, Mail Date May 22, 2009, Office Action.
U.S. Appl. No. 11/396,731, Mail Date Feb. 13, 2009, Office Action.
U.S. Appl. No. 11/396,731, Mail Date May 22, 2009, Office Action.
U.S. Appl. No. 11/406,203, Mail Date Mar. 3, 2009, Office Action.
U.S. Appl. No. 11/411,925, Mail Date Jan. 12, 2009, Office Action.
U.S. Appl. No. 11/427,297, Mail Date Jan. 30, 2009, Office Action.
U.S. Appl. No. 11/461,323, Mail Date May 2, 2007, Office Action.
U.S. Appl. No. 11/461,323, Mail Date Oct. 29, 2007, Office Action.
U.S. Appl. No. 11/461,323, Mail Date Apr. 25, 2008, Office Action.
U.S. Appl. No. 11/461,323, Mail Date Nov. 6, 2008, Office Action.
U.S. Appl. No. 11/532,325, Mail Date Feb. 23, 2009, Office Action.
U.S. Appl. No. 11/532,325, Mail Date Jun. 17, 2009, Office Action.
U.S. Appl. No. 11/744,089, Mail Date Nov. 26, 2008, Office Action.
U.S. Appl. No. 12/106,928, Mail Date Jan. 23, 2009, Office Action.
U.S. Appl. No. 12/106,937, Mail Date Mar. 30, 2009, Office Action.
U.S. Appl. No. 29/296,370, Mail Date Aug. 18, 2008, Office Action.
U.S. Appl. No. 29/296,370, Mail Date Dec. 2, 2008, Notice of Allowance.
U.S. Appl. No. 29/296,370, Mail Date Apr. 1, 2009, Notice of Allowance.
U.S. Appl. No. 10/264,306, Mail Date Aug. 13, 2009, Office Action.
U.S. Appl. No. 10/541,083, Mail Date Sep. 30, 2009, Notice of Allowance.
U.S. Appl. No. 10/616,832, Mail Date Jul. 21, 2009, Office Action.
U.S. Appl. No. 10/667,144, Mail Date Nov. 23, 2009, Office Action.
U.S. Appl. No. 10/787,073, Mail Date Aug. 13, 2009, Office Action.
U.S. Appl. No. 11/113,549, Mail Date Jul. 21, 2009, Office Action.
U.S. Appl. No. 11/198,811, Mail Date Sep. 22, 2009, Office Action.
U.S. Appl. No. 11/344,891, Mail Date Oct. 7, 2009, Office Action.
U.S. Appl. No. 11/396,141, Mail Date Aug. 26, 2009, Office Action.
U.S. Appl. No. 11/406,203, Mail Date Sep. 16, 2009, Office Action.
U.S. Appl. No. 11/411,925, Mail Date Sep. 10, 2009, Office Action.
U.S. Appl. No. 11/427,297, Mail Date Sep. 15, 2009, Office Action.
U.S. Appl. No. 11/461,323, Mail Date Jul. 27, 2009, Office Action.
U.S. Appl. No. 11/744,089, Mail Date Aug. 14, 2009, Office Action.
U.S. Appl. No. 11/958,295, Mail Date Aug. 27, 2009, Office Action.
U.S. Appl. No. 12/106,937, Mail Date Nov. 18, 2009, Office Action.
U.S. Appl. No. 12/106,928, Mail Date Oct. 5. 2009, Office Action.
U.S. Appl. No. 12/403,256, Mail Date Dec. 16, 2009, Restriction Requirement.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Mail Date Jan. 13, 2010, Notice of Allowance.
U.S. Appl. No. 10/356,214, Mail Date Jan. 13, 2010, Notice of Allowance.
U.S. Appl. No. 10/435,104, Mail Date Jan. 20, 2010, Notice of Allowance.
U.S. Appl. No. 10/517,004, Mail Date Jan. 11, 2010, Notice of Allowance.
U.S. Appl. No. 10/541,083, Mail Date Feb. 5, 2010, Notice of Allowance.
U.S. Appl. No. 10/616,832, Mail Date Jan. 11, 2010, Notice of Allowance.
U.S. Appl. No. 10/638,115, Mail Date Dec. 1, 2009, Notice of Allowance.
U.S. Appl. No. 10/682,459, Mail Date Dec. 23, 2009, Office Action.
U.S. Appl. No. 10/786,444, Mail Date Jan. 14, 2010, Office Action.
U.S. Appl. No. 10/787,073, Mail Date Feb. 17, 2010, Notice of Allowance.
U.S. Appl. No. 11/048,503, Mail Date Jan. 11, 2010, Notice of Allowance.
U.S. Appl. No. 11/455,993, Mail Date Feb. 17, 2009, Office Action.
U.S. Appl. No. 11/455,993, Mail Date Dec. 16, 2009, Office Action.
U.S. Appl. No. 11/532,325, Mail Date Jan. 5, 2010, Office Action.
U.S. Appl. No. 11/675,462, Mail Date Dec. 10, 2009, Office Action.
U.S. Appl. No. 11/959,334, Mail Date Aug. 19, 2009, Office Action.
U.S. Appl. No. 11/959,334, Mail Date Jan. 12, 2010, Notice of Allowance.
U.S. Appl. No. 29/296,370, Mail Date Feb. 10, 2010, Issue Notification.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.

U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 10/006,400, Mail Date Apr. 27, 2010, Notice of Allowance.
U.S. Appl. No. 10/006,400, Mail Date Aug. 2, 2010, Notice of Allowance.
U.S. Appl. No. 10/264,306, Mail Date Jan. 27, 2010, Office Action.
U.S. Appl. No. 10/264,306, Mail Date Jun. 15, 2010, Office Action.
U.S. Appl. No. 10/356,214, Mail Date May 13, 2010, Notice of Allowance.
U.S. Appl. No. 10/435,104, Mail Date Jul. 23, 2009, Notice of Allowance.
U.S. Appl. No. 10/435,104, Mail Date Jun. 2, 2010, Office Action.
U.S. Appl. No. 10/517,004, Mail Date Apr. 23, 2010, Notice of Allowance.
U.S. Appl. No. 10/517,004, Mail Date Aug. 3, 2010, Notice of Allowance.
U.S. Appl. No. 10/541,083, Mail Date May 10, 2010, Notice of Allowance.
U.S. Appl. No. 10/541,083, Mail Date Aug. 17, 2010, Notice of Allowance.
U.S. Appl. No. 10/616,832, Mail Date May 12, 2010, Notice of Allowance.
U.S. Appl. No. 10/616,832, Mail Date Sep. 20, 2010, Notice of Allowance.
U.S. Appl. No. 10/638,115, Mail Date Aug. 13, 2010, Notice of Allowance.
U.S. Appl. No. 10/638,115, Mail Date Aug. 13, 2010, Notice of Allowance.
U.S. Appl. No. 10/667,144, Mail Date Jun. 22, 2010, Office Action.
U.S. Appl. No. 10/669,313, Mail Date Oct. 31, 2005, Office Action.
U.S. Appl. No. 10/682,459, Mail Date Apr. 28, 2010, Office Action.
U.S. Appl. No. 10/787,073, Mail Date Aug. 25, 2010, Notice of Allowance.
U.S. Appl. No. 10/908,721, Mail Date Feb. 2, 2010, Office Action.
U.S. Appl. No. 11/048,503, Mail Date Apr. 26, 2010, Notice of Allowance.
U.S. Appl. No. 11/048,503, Mail Date Jul. 30, 2010, Notice of Allowance.
U.S. Appl. No. 11/113,549, Mail Date Jul. 6, 2010, Office Action.
U.S. Appl. No. 11/152,562, Mail Date Mar. 31, 2010, Office Action.
U.S. Appl. No. 11/152,562, Mail Date Sep. 16, 2010, Notice of Allowance.
U.S. Appl. No. 11/198,811, Mail Date Jun. 29, 2010, Notice of Allowance.
U.S. Appl. No. 11/316,775, Mail Date Apr. 16, 2008, Office Action.
U.S. Appl. No. 11/316,775, Mail Date Aug. 6, 2008, Office Action.
U.S. Appl. No. 11/344,891, Mail Date May 7, 2010, Office Action.
U.S. Appl. No. 11/390,586, Mail Date Jul. 6, 2010, Office Action.
U.S. Appl. No. 11/396,141, Mail Date May 4, 2010, Office Action.
U.S. Appl. No. 11/396,731, Mail Date Jun. 29, 2010, Office Action.
U.S. Appl. No. 11/406,203, Mail Date Jun. 18, 2010, Notice of Allowance.
U.S. Appl. No. 11/427,309, Mail Date May 28, 2008, Office Action.
U.S. Appl. No. 11/427,309, Mail Date Jan. 2, 2009, Office Action.
U.S. Appl. No. 11/427,309, Mail Date Apr. 20, 2009, Office Action.
U.S. Appl. No. 11/427,309, Mail Date Nov. 6, 2009, Office Action.
U.S. Appl. No. 11/427,309, Mail Date Apr. 26, 2010, Office Action.
U.S. Appl. No. 11/508,656, Mail Date Dec. 9, 2009, Office Action.
U.S. Appl. No. 11/508,656, Mail Date Mar. 25, 2010, Office Action.
U.S. Appl. No. 11/508,656, Mail Date Aug. 30, 2010, Office Action.
U.S. Appl. No. 11/508,662, Mail Date Dec. 28, 2009, Office Action.
U.S. Appl. No. 11/508,662, Mail Date Apr. 14, 2010, Office Action.
U.S. Appl. No. 11/508,715, Mail Date Jan. 6, 2010, Office Action.
U.S. Appl. No. 11/508,715, Mail Date Apr. 26, 2010, Office Action.
U.S. Appl. No. 11/532,576, Mail Date Mar. 1, 2010, Office Action.
U.S. Appl. No. 11/532,576, Mail Date Apr. 23, 2010, Office Action.
U.S. Appl. No. 11/674,930, Mail Date Jan. 8, 2009, Office Action.
U.S. Appl. No. 11/674,930, Mail Date Jun. 4, 2009, Office Action.
U.S. Appl. No. 11/674,930, Mail Date Jan. 8, 2010, Office Action.
U.S. Appl. No. 11/675,462, Mail Date Aug. 31, 2010, Office Action.
U.S. Appl. No. 11/757,108, Mail Date Nov. 25, 2009, Office Action.
U.S. Appl. No. 11/767,818, Mail Date Dec. 24, 2009, Office Action.
U.S. Appl. No. 11/767,818, Mail Date Mar. 22, 2010, Office Action.
U.S. Appl. No. 11/852,190, Mail Date Jun. 24, 2010, Office Action.
U.S. Appl. No. 11/958,281, Mail Date Sep. 2, 2010, Office Action.
U.S. Appl. No. 11/958,295, Mail Date May 25, 2010, Office Action.
U.S. Appl. No. 11/959,334, Mail Date Apr. 14, 2010, Notice of Allowance.
U.S. Appl. No. 11/959,334, Mail Date Jul. 23, 2010, Notice of Allowance.
U.S. Appl. No. 12/106,928, Mail Date May 10, 2010, Office Action.
U.S. Appl. No. 12/113,851, Mail Date Apr. 27, 2010, Office Action.
U.S. Appl. No. 12/113,851, Mail Date Jun. 24, 2010, Office Action.
U.S. Appl. No. 12/402,398, Mail Date Mar. 9, 2010, Office Action.
U.S. Appl. No. 12/402,398, Mail Date May 20, 2010, Office Action.
U.S. Appl. No. 12/403,256, Mail Date Mar. 30, 2010, Office Action.
U.S. Appl. No. 12/403,256, Mail Date Aug. 19, 2010, Notice of Allowance.
U.S. Appl. No. 12/403,277, Mail Date Jul. 8, 2010, Office Action.
U.S. Appl. No. 10/787,073, Mail Date Sep. 15, 2010, Issue Notification.
U.S. Appl. No. 11/427,297, Mail Date Sep. 15, 2010, Office Action.
U.S. Appl. No. 11/767,818, Mail Date Sep. 30, 2010, Office Action.
U.S. Appl. No. 12/365,397, Mail Date Sep. 13, 2010, Office Action.
U.S. Appl. No. 10/356,214, Mail Date Sep. 3, 2010, Notice of Allowance.
U.S. Appl. No. 10/435,104, Mail Date Oct. 5, 2010, Notice of Allowance.
U.S. Appl. No. 10/682,459, Mail Date Oct. 12, 2010, Office Action.
U.S. Appl. No. 11/406,203, Mail Date Oct. 6, 2010, Issue Notification.
U.S. Appl. No. 11/532,576, Mail Date Oct. 13, 2010, Notice of Allowance.
U.S. Appl. No. 11/958,281, Mail Date Oct. 8, 2010, Office Action.
U.S. Appl. No. 12/114,031, Mail Date Oct. 5, 2010, Office Action.
U.S. Appl. No. 12/403,277, Mail Date Oct. 12, 2010, Office Action.
U.S. Appl. No. 11/508,715, Mail Date Oct. 18, 2010, Office Action.
U.S. Appl. No. 10/264,306, Mail Date Oct. 29, 2010, Notice of Allowance.
U.S. Appl. No. 12/106,928, Mail Date Oct. 25, 2010, Office Action.
U.S. Appl. No. 11/198,811, Mail Date Oct. 20, 2010, Issue Notification.
U.S. Appl. No. 11/508,662, Mail Date Oct. 26, 2010, Office Action.
U.S. Appl. No. 11/852,190, Mail Date Nov. 1, 2010, Office Action.
U.S. Appl. No. 12/114,091, Mail Date Oct. 27, 2010, Office Action.
U.S. Appl. No. 10/435,104, Mail Date Jan. 12, 2011, Issue Notification.
U.S. Appl. No. 10/638,115, Mail Date Dec. 22, 2010, Issue Notification.
U.S. Appl. No. 11/113,549, Mail Date Jan. 4, 2011, Office Action.
U.S. Appl. No. 12/945,646, Mail Date Jan. 20, 2011, Office Action.
U.S. Appl. No. 12/402,398, Mail Date Jan. 24, 2010, Office Action.
U.S. Appl. No. 10/616,832, Mail Date Jan. 26, 2011, Issue Notification.
U.S. Appl. No. 11/152,562, Mail Date Jan. 26, 2011, Issue Notification.
U.S. Appl. No. 10/264,306, Mail Date Feb. 16, 2011, Issue Notification.

U.S. Appl. No. 11/767,818, Mail Date Feb. 16, 2011, Office Action.
U.S. Appl. No. 10/517,004, Mail Date Nov. 23, 2010, Issue Notification.
U.S. Appl. No. 10/541,083, Mail Date Dec. 1, 2010, Issue Notification.
U.S. Appl. No. 11/048,503, Mail Date Dec. 8, 2010, Issue Notification.
U.S. Appl. No. 11/959,334, Mail Date Nov. 10, 2010, Issue Notification.
U.S. Appl. No. 12/114,031, Mail Date Nov. 22, 2010, Office Action.
U.S. Appl. No. 12/403,256, Mail date Nov. 23, 2010, Issue Notification.
U.S. Appl. No. 12/113,851, Mail Date Dec. 16, 2010, Office Action.
U.S. Appl. No. 12/114,091, Mail Date Dec. 17, 2010, Office Action.
U.S. Appl. No. 11/427,309, Mail Date Nov. 15, 2010, Office Action.

* cited by examiner

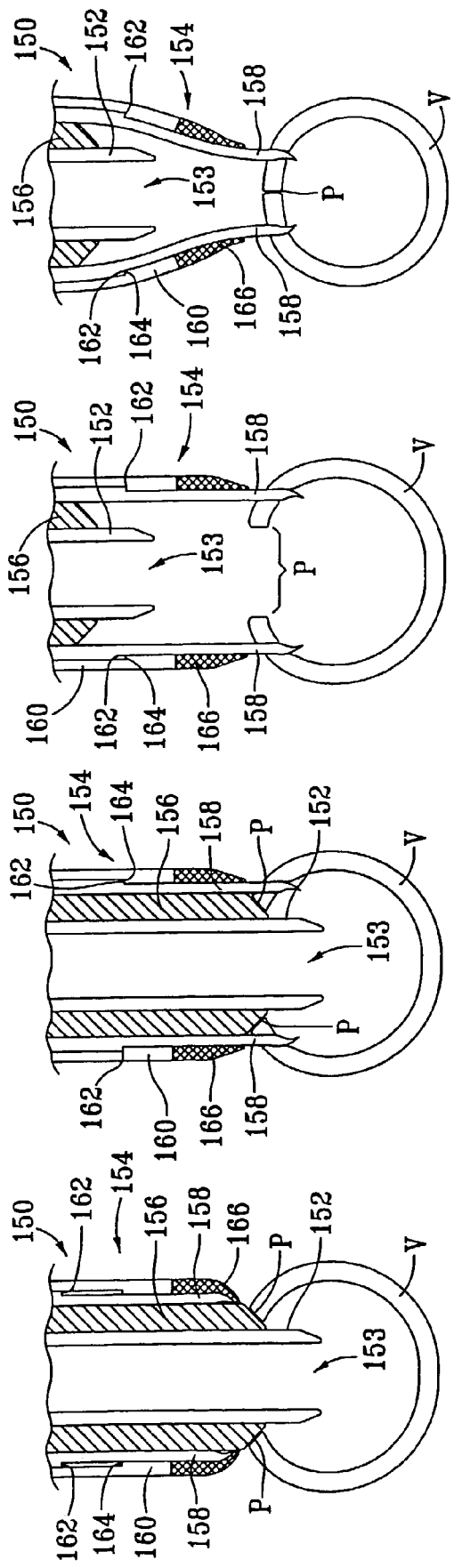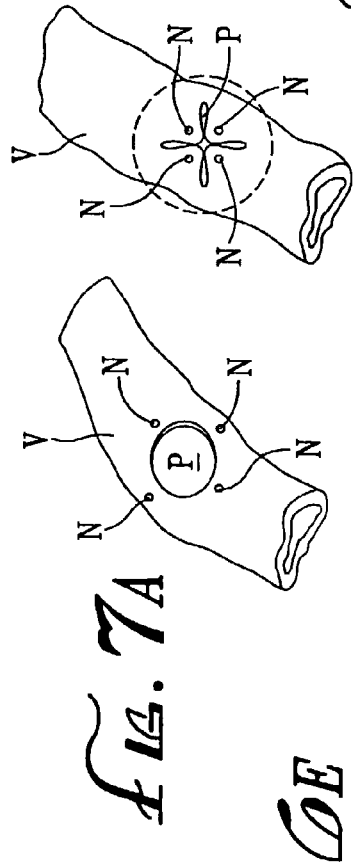

INTEGRATED VASCULAR DEVICE WITH PUNCTURE SITE CLOSURE COMPONENT AND SEALANT AND METHODS OF USE

REFERENCE TO RELATED APPLICATION

This application is a continuation of U.S. patent application Ser. No. 09/610,238 filed on Jul. 5, 2000, which will issue as U.S. Pat. No. 6,391,048 on May 21, 2002, which is a continuation-in-part of prior application Ser. No. 09/478,179 filed on Jan. 5, 2000, will issued as U.S. Pat. No. 6,197,042 on Mar. 6, 2001.

FIELD OF THE INVENTION

The present invention relates to apparatus and methods for sealing an iatrogenic puncture in a vessel formed in conjunction with a diagnostic or therapeutic treatment. More particularly, the present invention provides an integrated vascular device comprising a sheath having a puncture closure component and puncture sealant.

BACKGROUND OF THE INVENTION

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel and issues of biocompatibility.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The use of backbleed indication as a positioning technique within a vascular puncture is known. For example, U.S. Pat. No. 4,317,445 to Robinson describes a flashback chamber for providing visual indication of venous entry of a cannula. However, that device does not discuss vascular wound closure. U.S. Pat. No. 5,676,689 to Kensey et al., which claims priority from the U.S. Pat. No. 5,222,974 patent discussed above, uses a vessel location device to simplify positioning of the biodegradable plug. The vessel locator enables blood from the vessel to flow there through so that the position of the vessel may be determined. However, the Kensey system only proffers one closure device, and that device is complex and raises concerns about biocompatibility. It also requires the closure component to be positioned within the puncture, thereby increasing the likelihood of dangerous over-advancement of the plug into the vessel.

The percutaneous puncture closure devices described in the foregoing patents generally have the drawback that they require relatively complex mechanisms and require time consuming manipulation to achieve hemostasis. It therefore would be desirable to provide apparatus and methods suitable for vascular puncture closure that overcome these disadvantages of previously known devices.

It also would be desirable to provide apparatus and methods that quickly and effectively achieve hemostasis.

It further would be desirable to provide apparatus and methods wherein all foreign materials left in a patient's body are bioabsorbable.

It still further would be desirable to provide vascular puncture closure apparatus and methods that are safe, low cost, and easy to use.

SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It further is an object of the present invention to provide apparatus and methods wherein all foreign materials left in a patient's body are bioabsorbable.

It still further is an object of the present invention to provide vascular puncture closure apparatus and methods that are safe, low cost, and easy to use.

These and other objects of the present invention are accomplished by providing an integrated vascular device comprising a sheath having a puncture closure component and puncture sealant. The closure component is disposed on and advanceable over the exterior of the sheath, which may, for example, comprise an introducer sheath, a trocar, or a catheter. The closure component may comprise any of a variety of apparatus suited to close a vascular puncture. Once the closure component has been actuated to close the puncture, sealant is introduced to the exterior surface of the closed puncture, preferably through the sheath's interior lumen, where the sealant seals the puncture closed. The sheath with closure component is then removed from the patient.

In a preferred embodiment constructed in accordance with the present invention, the closure component comprises a twist closure device. The device pierces tissue surrounding the vascular puncture and then is rotated to close the wound. In an alternative embodiment, the closure component comprises needles and an elastic segment surrounding the needles. The needles pierce the puncture with the elastic segment expanded. The segment is then allowed to resiliently contract to an unstressed configuration of smaller diameter, thereby drawing the needles together and closing the wound.

In a still further alternative embodiment, the needles, or prongs, are elastically deformed to an expanded diameter, in which they pierce the tissue adjacent to puncture. The needles then are allowed to resiliently contract to an unstressed configuration of smaller diameter, thereby closing the wound.

Sealant then may be introduced, preferably through the interior lumen of the sheath, to seal the puncture closed. The sealant may comprise any of a variety of sealants, per se known, including adhesives, sutures, and clips, all of which are preferably bioabsorbable. Alternatively, the closure component may further comprise the sealant, wherein the closure component is left in place within the vessel until hemostasis naturally occurs, or wherein the closure component comprises a monopolar electrode or opposed bipolar electrodes that cauterize the wound with RF current. In addition to cauterization, RF energy generates heat that beneficially causes shrinkage of the vascular tissue, thereby assisting closure of the wound. Thermal energy from electrical induction, infrared light, ultrasonic vibration, microwave or laser irradiation, and other means may also be used to seal the puncture.

Advantageously, the puncture closure component of the present invention is inexpensively integrated into a sheath, thereby minimizing mechanical complexity while providing quick, safe, effective, and easy-to-use apparatus for achieving vascular closure that overcomes drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 6A-6E are side-sectional views of a further alternative embodiment in use at a vascular puncture site, illustrating a method of sealing the puncture site; and FIGS. 7A and 7B are isometric views of a section of vessel including and corresponding to the vascular puncture site of FIG. 6, further illustrating the method of FIG. 6.

DETAILED DESCRIPTION OF THE INVENTION

The integrated vascular sheath with closure component of the present invention overcomes disadvantages associated with previously known methods and apparatus for sealing a vascular puncture by providing a quick, simple, safe, low cost, effective, and easy-to-use solution to wound closure. Apparatus constructed in accordance with the present invention provide vascular access and wound closure in a single device, eliminating the time and manipulation required to insert a separate closure device at the completion of a procedure.

Figure 1:
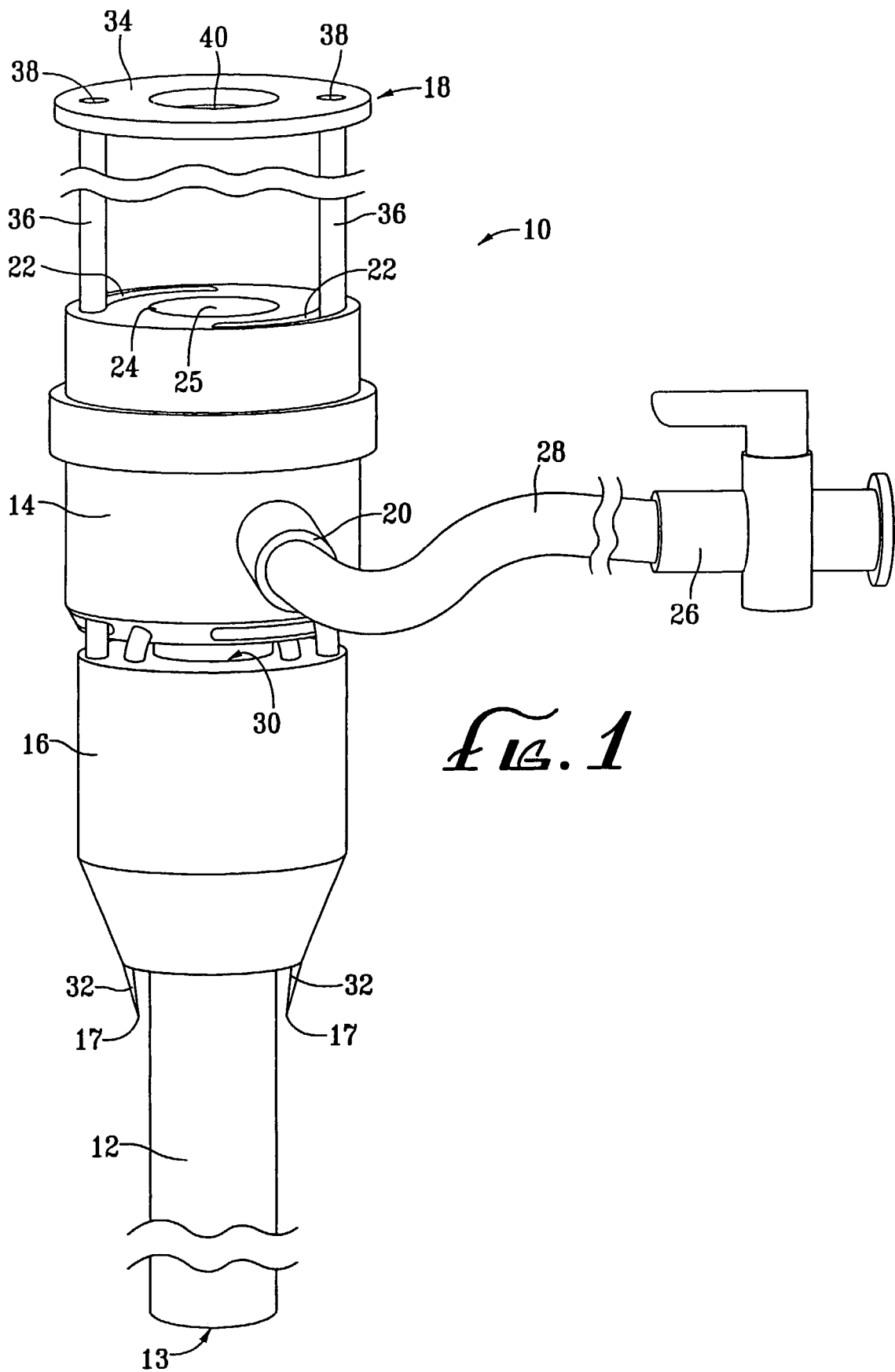
FIG. 1 is a side view of a preferred embodiment of an integrated vascular device constructed in accordance with the present invention.

Referring to FIG. 1, a first embodiment of apparatus of the present invention is described. Vascular device 10 comprises sheath 12 coupled to hub 14, closure component 16, and closure actuator 18.

Sheath 12, which may, for example, comprise an introducer sheath, a trocar, or a catheter, includes central lumen 13 through which other devices may be introduced into the vasculature, for example, to perform a diagnostic or interventional procedure such as angiography, angioplasty, or stenting, or to seal a puncture site.

Hub 14 is mounted on the proximal end of sheath 12 and includes side port 20, arc lumens 22, and device port 24. Device port 24 communicates with central lumen 13 of sheath 12, and has self-sealing elastomeric membrane 25 disposed across it. Self-sealing membrane 25, which may comprise, for example, latex or a biocompatible synthetic rubber, permits interventional devices to be introduced through device port 24, while preventing blood loss through central lumen 13. Side port 20 of hub 14 is also in communication with central lumen 13, and is connected to hemostatic port 26 via biocompatible tubing 28.

In accordance with the principles of the present invention, closure component 16 comprises lumen 30 that receives sheath 12. Component 16 is slidably disposed on the exterior of sheath 12 and is movable from a stowed position, adjacent hub 14, to a distal deployment position, where tines 17 of component 16 are urged into engagement with tissue surrounding a vascular puncture. Closure component 16 comprises at least two sharpened tips, or tines 17. Tines 17 preferably comprise backbleed ports 32. Closure component 16 is rotatable within arc-lumens 22 about the longitudinal axis of sheath 12, so that, with tines 17 engaging tissue surrounding the vascular puncture, component 16 closes the puncture.

Closure actuator 18 comprises plunger 34 and tubes 36, which are configured to slidably pass through arc lumens 22 of hub 14. The proximal ends of tubes 36 are coupled to backbleed bores 38 of plunger 34. The distal ends of tubes 36 are mounted, either permanently or detachably, in closure component 16, so that movement of plunger 34 causes corresponding proximal or distal movement of closure component 16. Likewise, rotation of plunger 34 causes corresponding rotation of tubes 36 within arc lumens 22, which, in turn, rotates closure component 16 about the longitudinal axis of sheath 12.

Plunger 34 further comprises device bore 40, coaxially aligned with device port 24, and through which interventional devices or puncture sealants may be passed. As described in detail hereinafter, when plunger 34 is moved to its proximal-most position, closure component 16 is disposed adjacent to hub 14 and preferably provides adequate clearance for interventional devices to be inserted through device port 24 and central lumen 13 into the patient's vasculature. When moved to its distal-most position, plunger 34 causes tubes 36 to urge closure component 16 distally. Interventional devices or sealants then may be introduced through device bore 40, device port 24, and central lumen 13 into the vasculature.

Backbleed bores 38 of plunger 32 are in communication with backbleed lumens (not shown) within tubes 36. The backbleed lumens of tubes 36 are in communication with backbleed ports 32 of tines 17, thereby establishing a complete backbleed path through ports 32, the lumens (not shown) of tubes 36, and bores 38. When tines 17 of closure component 16 pierce a vessel wall surrounding a vascular puncture, blood enters backbleed ports 32 and exits through backbleed bores 38, providing visual confirmation to a surgeon that tines 17 are positioned within the vessel wall. The backbleed path thus enables the surgeon to determine when closure component 16 has been sufficiently advanced to permit rotation of component 16 to close the puncture, while reducing the risk that component 16 is either short of the puncture site or is extended into the vessel.

In conjunction with closure of the puncture site caused by rotation of component 16, a puncture sealant may be introduced to the puncture site to seal the site closed. The sealant may, for example, comprise an adhesive, such as a bioglue, tissue sealant, or clotting agent, delivered through hemostatic port 26, biocompatible tubing 28, side port 20 and central lumen 13 of introducer sheath 12 to the vascular puncture to further help seal the vessel after puncture closure with closure component 16. Alternatively, the adhesive may be delivered through device port 24 or through the backbleed path described above. Instead of adhesives, the closure component may further comprise the sealant, wherein the closure component is left in place within the vessel until hemostasis naturally occurs. The sealant may also comprise sutures delivered through central lumen 13. Additionally, the sealant may comprise thermal energy application from, for example, electrical induction, infrared light, ultrasonic vibration, microwave or laser irradiation, and other means.

Figure 2:
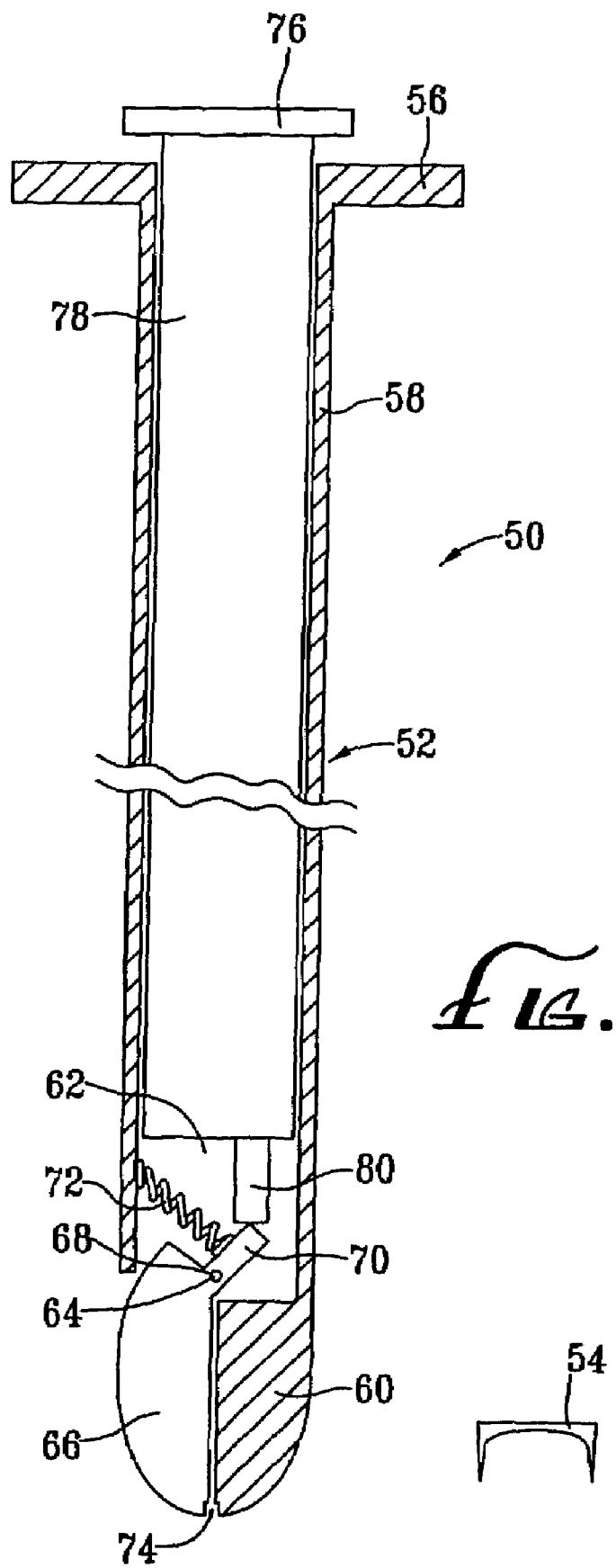
FIG. 2 is a side-sectional view of a sealing device for use with the vascular device of FIG. 1.

With reference to FIG. 2, an alternative puncture sealing device in accordance with the present invention is described. Sealing device 50 comprises delivery device 52 and clip 54. Delivery device 52 comprises proximal end 56 attached to tube 58. Tube 58 terminates at first jaw 60 at its distal end and further comprises lumen 62 and pin 64. Pin 64 extends into lumen 62 from an interior surface of tube 58 and is disposed perpendicular to the longitudinal axis of tube 58.

Delivery device 52 further comprises second jaw 66 having female connector 68 coupled to pin 64, so that second jaw 66 pivots about pin 64. Second jaw 66 further comprises moment arm 70. Tension spring 72 is coupled to moment arm 70 and to the interior surface of tube 58 in a manner that biases second jaw 66 against first jaw 60.

First jaw 60 and second jaw 66 preferably form channel 74 when biased against one another. Channel 74 is configured to receive clip 54. The biasing force applied by tension spring 72 holds clip 54 within channel 74, so that the clip may be advanced into tissue surrounding a vascular puncture that has had its edges approximated by closure component 16.

Delivery device 52 still further comprises plunger 76 coupled to pushrod 78 having release arm 80. Pushrod 78 is received within lumen 62 of tube 58, so that release arm 80 engages moment arm 70.

Distal advancement of pushrod 78, via application of force to plunger 76, causes release arm 80 to urge moment arm 70 distally. This motion overcomes the biasing force applied by tension spring 72 and causes second jaw 66 to pivot about pin 64. Second jaw 66 thus no longer contacts first jaw 60, and clip 54 is released from channel 74. Tube 58, first jaw 60, second jaw 66, and clip 54 of sealing device 50 preferably are sized for introduction into a patient's vasculature through device bore 40, device port 24, and lumen 13 of vascular device 10.

Referring to FIGS. 3A-3D through 4A-4D, in conjunction with FIGS. 1 and 2, a method of using vascular device 10 with sealing device 50 is described. Sheath 12 is advanced through skin, fat, and muscle tissue into vessel V, through the vessel wall tissue surrounding vascular puncture P. With plunger 34 and tubes 36 of actuator 18 in the proximal-most, fully retracted position, an interventional procedure is performed by introducing one or more interventional devices, e.g. angioplasty balloons, stent delivery systems, atherectomy devices, etc., through device port 24 and lumen 13 of sheath 12, in accordance with well-known techniques. Side port 20 may be used to infuse fluids, e.g., contrast agents or medications, into the vessel through sheath 12 during the interventional procedure.

Upon completion of the procedure, vascular device 10 may be advantageously used to close vascular puncture P. At this point, closure actuator 18 and closure component 16 are disposed in the proximal-most position, with component 16 adjacent to hub 14. Closure actuator 18 is advanced by urging plunger 34 in the distal direction, thus causing tubes 36 to slide through arc lumens 22 of hub 14 and advance closure component 16.

Figure 3A:
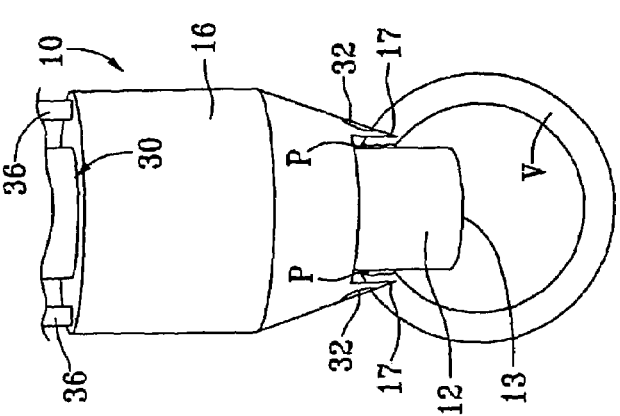
FIGS. 3A-3D are side views of the closure component of FIG. 1 in use at a vascular puncture site, shown in section, with the sealing device of FIG. 2, illustrating a method of sealing the puncture site.
Figure 4A:
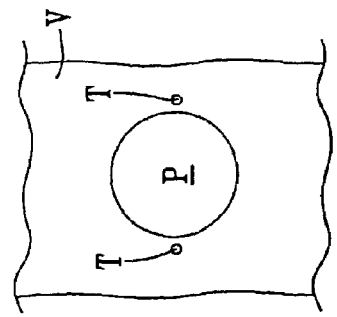
FIGS. 4A-4D are top views of the vascular puncture site of FIG. 3, corresponding to the side-sectional views of FIG. 3, further illustrating the method of FIG. 3.

As seen in FIG. 3A, continued distal advancement of plunger 34 causes tines 17 at the distal end of closure component 16 to pierce tissue surrounding puncture P, so that the backbleed ports 32 of tines 17 directly communicate with the puncture wound. Tine punctures T in FIG. 4A represent the points at which tines 17 enter vessel V. The presence of pressure in the vessel higher than atmospheric pressure causes blood to pass through backbleed ports 32, through the backbleed lumens (not shown) of tubes 36, and exit through the proximal ends of backbleed bores 38, thus confirming that tines 17 have engaged tissue around the puncture site and should not be advanced further.

Figure 3B:
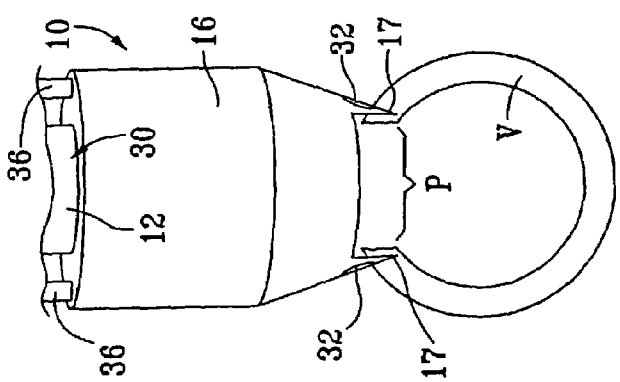
Figure 4B:
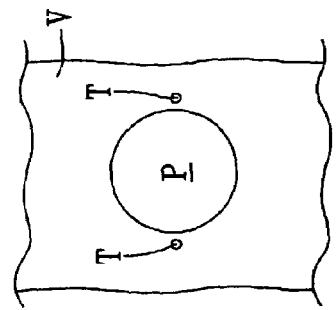
Figure 3C:
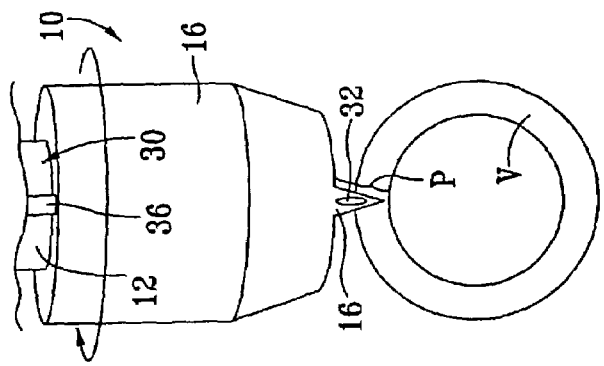
Figure 4C:
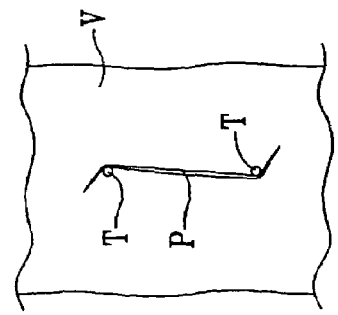

In FIG. 3B, sheath 12 is removed from puncture P to facilitate closure of the puncture. Closure actuator 18 is held stationary while hub 14 is withdrawn proximally, thereby withdrawing sheath 12 proximally from puncture P. The puncture remains open, as seen in FIG. 4B. With sheath 12 no longer within puncture P, closure actuator 18 is rotated within arc lumens 22 to rotate closure component 16. Rotation of closure component 16 causes tines 17 to rotate and urge the puncture closed, as seen in FIGS. 3C and 4C.

Upon closure of puncture P, a sealant is introduced to seal the wound closed. The sealant may, for example, comprise an adhesive, such as a bioglue, tissue sealant, or clotting agent, it may comprise a suture, it may comprise thermal energy application, or it may comprise leaving the closure component in place within vessel V until hemostasis naturally occurs. Alternatively, the sealing device may comprise a clip, as described hereinafter.

Figure 3D:
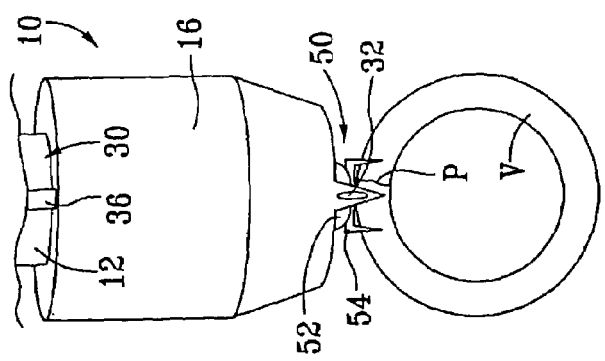
Figure 4D:
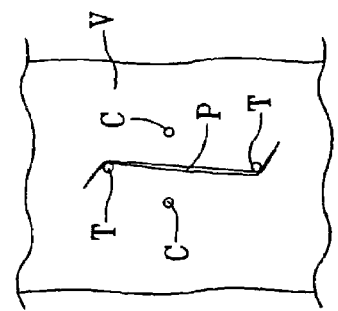

FIGS. 3D and 4D show apparatus 10 used in conjunction with sealing device 50 of FIG. 2. With clip 54 disposed in channel 74 of delivery device 52, the delivery device is delivered to vessel V through device bore 40 of closure actuator 18, device port 24 of hub 14, and central lumen 13 of sheath 12. Clip 54 punctures the vessel at tissue surrounding closed puncture P, creating clip punctures C and sealing the puncture. Pushrod 78 of delivery device 52 is then actuated to separate second jaw 66 from first jaw 60 to release clip 54 from delivery device 52. Apparatus 10 and delivery device 52 are removed from the patient to complete the procedure. Clip 54 maintains closure until hemostasis occurs and is preferably bioabsorbable so that no foreign materials are permanently implanted in the patient's body. Additional clips may also be implanted, as required.

Figures 5A, 5B, 5C:
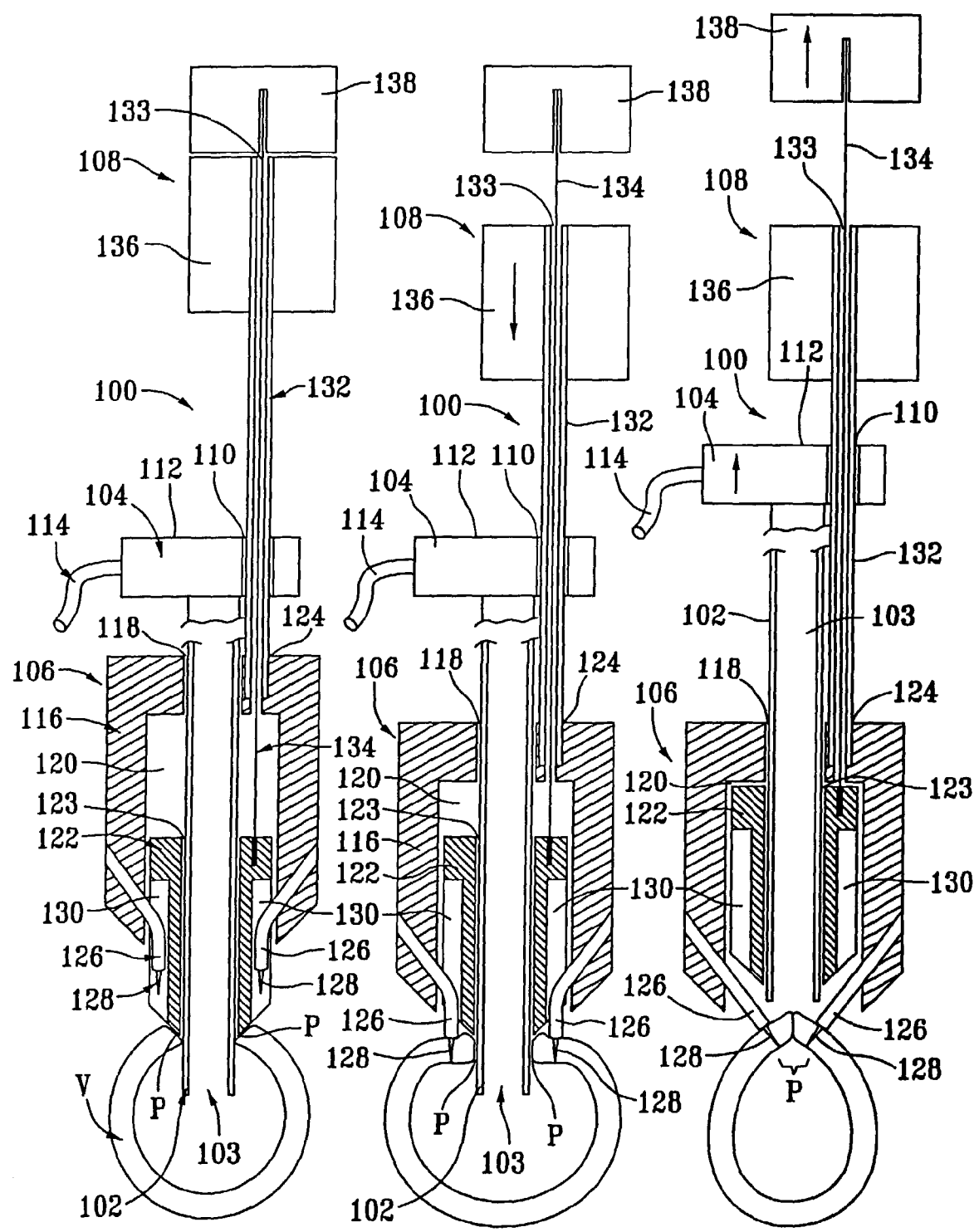
FIGS. 5A-5C are side-sectional views of an alternative embodiment of an integrated vascular device of the present invention in use at a vascular puncture site, illustrating a method of sealing the puncture site.

With reference now to FIGS. 5A-5C, an alternative integrated vascular device in accordance with the present invention is described. Apparatus 100 comprises sheath 102 coupled to hub 104, closure component 106, and closure actuator 108.

Like sheath 12, sheath 102 may, for example, comprise an introducer sheath, a trocar, or a catheter, and includes central lumen 103 through which other devices may be introduced into the vasculature, for example, to perform a diagnostic or interventional procedure such as angiography, angioplasty, or stenting, or to seal a puncture site. Hub 104 comprises bore 110, which slidably receives actuator 108, and device port 112, which is in communication with central lumen 103 of sheath 102 and permits introduction of interventional devices while preventing blood loss through central lumen 103. Hub 104 further comprises side port 114.

Closure component 106 comprises outer housing 116 having lumen 118 configured to slidably receive sheath 102, bore 120 for slidably receiving inner housing 122, lumen 124 adapted to receive closure actuator 108, and needles or prongs 126 with sharpened tips 128. Inner housing 122 has lumen 123 adapted to receive sheath 102 and channels 130 adapted to receive prongs 126. Component 106 comprises at least two prongs 126, and preferably comprises four.

Closure actuator 108 comprises actuation tube 132 having lumen 133, actuation rod 134 disposed within actuation tube 132, first plunger 136 coupled to the proximal end of tube 132, and second plunger 138 coupled to the proximal end of rod 134. The distal end of tube 132 is affixed, either permanently or detachably, in lumen 124 to outer housing 116 of closure component 106, while the distal end of rod 134 is coupled to inner housing 122.

To perform an interventional procedure through central lumen 103 of sheath 102, the sheath is advanced through skin, fat, and muscle tissue into vessel V, through vascular puncture P, in accordance with well-known techniques. With closure component 106 in the proximal-most, fully retracted position adjacent hub 104, the interventional procedure then is performed by introducing one or more interventional devices, e.g. angioplasty balloons, stent delivery systems, atherectomy devices, etc., through device port 112 and lumen 103 of sheath 102, again in accordance with well-known techniques.

Side port 114 may be used to infuse fluids, e.g., contrast agents or medications, into the vessel through sheath 102 during the interventional procedure.

Upon completion of the procedure, apparatus 100 advantageously may be used to close the vessel. Closure component 106 is advanced distally by urging plungers 136 and 138 distally. Inner housing 122 is only partially received within bore 120 of outer housing 116 so that prongs 126 are elastically deformed and received within channels 130. As shown in FIG. 5A, closure component 106 is advanced until inner housing 122 abuts against the vessel V, as may be determined, for example, with a backbleed indicator (not shown).

In FIG. 5B, first plunger 136 is urged distally to distally advance actuation tube 132 and outer housing 116, while second plunger 138 and sheath 102 are held stationary. Advancement of outer housing 116 advances sharpened tips 128 of prongs 126 into tissue surrounding puncture P.

In FIG. 5C, sheath 102 and second plunger 138 are retracted proximally to draw sheath 102 out of vessel V and to draw inner housing 122 completely within bore 120 of outer housing 116. Proximally retracting inner housing 122 via actuation rod 134 and second plunger 138 removes prongs 126 of outer housing 116 from channels 130 of the inner housing. The prongs resiliently contract to a lower stress configuration, thereby drawing opposing sides of puncture P together and closing the wound. A sealant, for example clip 54 of FIG. 2, may then be introduced to the closed puncture to seal the site closed, as discussed hereinabove. Alternatively, the sealing device may comprise RF current, supplied by an RF generator (not shown), applied across opposed tips 128, which act as bipolar electrodes.

Referring to FIGS. 6A-6E, as well as FIGS. 7A and 7B, a still further alternative embodiment of apparatus of the present invention is described. FIG. 6 depict the closure component of an integrated vascular device in use at vascular puncture P within vessel V. Apparatus 150 comprises sheath 152 coupled to a hub (not shown), closure component 154, and a closure actuator (not shown). Various closure actuators for use with closure component 154 will be apparent to those of skill in the art from the foregoing embodiments.

Sheath 152 may, for example, comprise an introducer sheath, a trocar, or a catheter, and includes central lumen 153 through which other devices may be introduced into the vasculature, for example, to perform a diagnostic or interventional procedure such as angiography, angioplasty, or stenting, or to seal a puncture site. Closure component 154 comprises spacer 156, needles 158, and needle cover 160. Spacer 156 is coaxially and slidably disposed about the exterior of sheath 152, and preferably has an annular diameter of about 1 mm to ensure that needles 158 engage the tissue surrounding puncture P rather than enter the puncture, so that the needles are able to draw the wound closed, as described hereinbelow. Needles 158 are disposed between spacer 156 and cover 160 during advancement to puncture P. Needles 158 comprise ledges 162, which act as positive stops to prevent excessive advancement of the needles with respect to cover 160, which comprises corresponding annular ledge 164. Cover 160 further comprises elastic segment 166, configured to elastically deform needles 158. Closure component 154 comprises at least two needles 158, and preferably comprises four. Needles 158 may further comprise retaining means (not shown), such as barbs or hooks, to assist in gripping tissue.

As shown in FIG. 6A, sheath 152 may be advanced through skin, fat, and muscle tissue into vessel V, through vascular puncture P, in accordance with well-known techniques. With closure component 154 in a proximal-most, fully retracted position adjacent the hub, an interventional procedure is performed through central lumen 153 of sheath 152 by introducing one or more interventional devices through the lumen into the patient's vasculature. Closure component 154 then is advanced via the closure actuator until it abuts against vessel V, as may be determined, for example, with a backbleed indicator, such as described for the foregoing embodiments. Cover 160 protects needles 158 and prevents snagging of tissue as closure component 154 is distally advanced down sheath 152 and through skin, fat, and muscle tissue. Spacer 156 retains needles 158 in a position away from the edge of puncture P.

In FIG. 6B, needles 158 are distally advanced with respect to needle cover 160 until ledge 162 abuts ledge 164. Needles 158 deflect elastic segment 166 of cover 160 outward and pierce tissue surrounding puncture P. FIG. 7A depicts, in isometric view, the segment of vessel V surrounding puncture P. With a needle arrangement comprising four needles 158, the needles create needle punctures N surrounding vascular puncture P. Sheath 152 and spacer 156 then are retracted proximally and removed from vessel V, as shown in FIG. 6C. As depicted in FIGS. 6D and 7B, elastic segment 166 of needle cover 160 resiliently contracts, thereby drawing needles 158 together and approximating the edges of the wound.

A sealant, such as a bioglue, tissue sealant, or clotting agent, then may be introduced to the puncture site to seal the wound closed. Alternatively, closure component 154 may be maintained in position until hemostasis occurs naturally, or sutures may be introduced through central lumen 153. In addition, or in the alternative, RF energy may be applied across needles 158, as described hereinabove with respect to FIG. 5, or a clip, such as clip 54 of sealing device 50 of FIG. 2, may be applied. Thermal energy from electrical induction, infrared light, ultrasonic vibration, microwave or laser irradiation, and other means may also be used to seal the puncture.

Illustratively, FIG. 6E depicts sealing device 170, comprising adhesive 172, being delivered through central lumen 153 within delivery sheath 174. After sufficient time for adhesive 172 to set, apparatus 150 is removed from vessel V.

Although preferred illustrative embodiments of the present invention are described hereinabove, it will be evident to one skilled in the art that various changes and modifications may be made without departing from the invention. It is intended in the appended claims to cover all such changes and modifications that fall within the true spirit and scope of the invention.

What is claimed is:

1. An apparatus for approximating opposing edges of a puncture in a vessel wall of a vessel comprising:
   a tubular member having a longitudinal axis, proximal and distal regions, an exterior surface, and a lumen extending along an entire length of the tubular member, the lumen being adapted to receive and introduce another device from the proximal region through the lumen and the distal region to the vessel;
   a first closure component comprising at least two sharpened tips for engagement of the vessel wall and a lumen to receive the tubular member, the closure component being rotatable and slidable about the longitudinal axis and the exterior surface of the tubular member proximal of the puncture to the vessel wall, the first closure component configured to selectively close the puncture and being movable with the tubular member;
   a closure actuator coupled to the first closure component, the closure actuator configured to move relative to the tubular member to advance the first closure component from a region on the tubular member proximal of the puncture to the vessel wall, configured to urge the first closure component into engagement with the vessel wall and configured to rotate the first closure component on the exterior surface of the tubular member and about the longitudinal axis to urge the opposing edges of the puncture into a closed position, the first closure component configured to selectively close the puncture and being movable with the closure actuator; and
   a second closure component configured to maintain the closed position of the puncture, the second closure component being configured to maintain the closed position of the puncture following removal of the first closure component and the tubular member.

2. The apparatus according to claim 1, wherein the first closure component and/or the second closure component further comprises at least two resilient prongs, wherein the sharpened tips are disposed on the distal ends of the prongs.

3. The apparatus of claim 2, wherein the prongs have an expanded delivery configuration configured for engagement of the vessel wall in a vicinity of the puncture, and a deployed configuration, wherein the prongs resiliently retract to close the puncture.

4. The apparatus of claim 2, further comprising a sealing component selected from a group consisting of RF energy, thermal energy, electrical induction, infrared light, ultrasonic vibration, microwave or laser irradiation, clips, sutures, and combinations thereof 5. The apparatus of claim 4, wherein the sealing component is associated with the resilient prongs.

6. The apparatus of claim 1, wherein the first closure component and/or the second closure component is constructed of a bioabsorbable material.

7. The apparatus of claim 4, the second closure component comprising the sealing component.

8. The apparatus of claim 2, further comprising a sealing component including adhesives.

9. The apparatus of claim 1, wherein each sharpened tip further comprises a backbleed port.

10. An apparatus for approximating opposing edges of a puncture in a vessel wall of a vessel comprising:
    a tubular member having a longitudinal axis, proximal and distal regions, an exterior surface, and a lumen extending along an entire length of the tubular member, the lumen being adapted to receive and introduce another device from the proximal region through the lumen and the distal region to the vessel;
    a closure component comprising at least two sharpened tips for engagement of the vessel wall and a lumen to receive the tubular member, two sharpened tips of the at least two sharpened tips being disposed on opposite sides of the closure component and being separated by a first distance, the closure component being rotatable about the longitudinal axis and disposed and slidable about the exterior surface of the tubular member proximal of the puncture to the vessel wall, the two sharpened tips being separated by the first distance following rotation of the closure component relative to the longitudinal axis;
    a closure actuator coupled to the closure component, the closure actuator configured to move relative to the tubular member to advance the closure component from a region on the tubular member proximal of the puncture to the vessel wall, configured to urge the closure component into engagement with the vessel wall and configured to rotate the closure component on the exterior surface of the tubular member and about the longitudinal axis to urge the opposing edges of the puncture into a closed position; and a second closure component configured to maintain the closed position of the puncture, the second closure component being deployed through the lumen of the first closure component and being configured to maintain the closed position of the puncture following removal of the first closure component and the tubular member.

11. The apparatus of claim 10, further comprising a sealing component selected from a group consisting of RF energy, thermal energy, electrical induction, infrared light, ultrasonic vibration, microwave or laser irradiation, clips, sutures, and combinations thereof.

12. The apparatus of claim 10, wherein each sharpened tip further comprises a backbleed port.

13. The apparatus of claim 12, further comprising a tube extending from the closure actuator to the closure component, the tube communicating with the backbleed port.

14. The apparatus of claim 13, further comprising a hub mounted to the tubular member, the hub including two arc lumens cooperating with the closure actuator.

15. The apparatus of claim 14, wherein the two arc lumens receive the tube extending from the closure actuator to the closure component.

16. An apparatus for approximating opposing edges of a puncture in a vessel wall of a vessel comprising:

a tubular member having a longitudinal axis, proximal and distal regions, an exterior surface, and a lumen extending along an entire length of the tubular member, the lumen being adapted to receive and introduce another device from the proximal region through the lumen and the distal region to the vessel;

a first closure component comprising at least two sharpened tips for engagement of the vessel wall and a lumen to receive the tubular member, two sharpened tips of the at least two sharpened tips being disposed on opposite sides of the closure component and being separated by a first distance, the first closure component being rotatable and slidable about the longitudinal axis and the exterior surface of the tubular member proximal of the puncture to the vessel wall, the two sharpened tips being separated by the first distance following rotation of the closure component relative to the longitudinal axis, the first closure component selectively closing the puncture; and a closure actuator coupled to the closure component, the closure actuator movable relative to the tubular member to advance the first closure component from a region on the tubular member proximal of the puncture to the vessel wall, to urge the first closure component into engagement with the vessel wall and to rotate the first closure component on the exterior surface of the tubular member and about the longitudinal axis to urge the opposing edges of the puncture into a closed position, the first closure component being removable with the tubular member and the closure actuator; and a second closure component configured to maintain the closed position of the puncture following removal of the first closure component and the tubular member, the second closure component being deployed from within the lumen.

17. The apparatus of claim 16, wherein the second closure component comprises an adhesive, tissue sealant, or clotting agent delivered through the lumen.

18. The apparatus of claim 16, further comprising a second closure component delivery device disposable through the lumen.

19. The apparatus of claim 16, further comprising a backbleed path extending from the tines to a proximal end of the closure actuator.

20. The apparatus of claim 16, wherein the distance is smaller than an outer diameter of the first closure component.

* * * * *